United States Patent
Hassidov et al.

(10) Patent No.: US 10,925,466 B2
(45) Date of Patent: Feb. 23, 2021

(54) APPARATUS AND METHOD FOR COUPLING BETWEEN A COLONOSCOPE AND ADD-ON TUBES

(71) Applicant: Motus GI Medical Technologies Ltd., Tirat HaCarmel (IL)

(72) Inventors: Noam Hassidov, Moshav Bustan HaGalil (IL); Boris Shtul, Kiryat-Yam (IL); Eyal Kochavi, Haifa (IL); Tzach Arnon, Yodfat (IL); Koby Luleko, Eshchar (IL); Dan Blecher, Bamat-Gan (IL)

(73) Assignee: Motus GI Medical Technologies Ltd., Tirat HaCarmel (IL)

( * ) Notice: Subject to any disclaimer, the term of this patent is extended or adjusted under 35 U.S.C. 154(b) by 0 days.

(21) Appl. No.: 15/959,397

(22) Filed: Apr. 23, 2018

(65) Prior Publication Data

US 2018/0235448 A1 Aug. 23, 2018

Related U.S. Application Data

(60) Division of application No. 15/108,601, filed as application No. PCT/IL2015/050615 on Jun. 17, (Continued)

(51) Int. Cl.
*A61B 1/00* (2006.01)
*A61B 1/31* (2006.01)
(Continued)

(52) U.S. Cl.
CPC ........ *A61B 1/00135* (2013.01); *A61B 1/0014* (2013.01); *A61B 1/00089* (2013.01); (Continued)

(58) Field of Classification Search
CPC ............ A61B 1/00089; A61B 1/00112; A61B 1/00135; A61B 1/0014; A61B 1/00142; A61B 1/00154; A61B 2017/00296
See application file for complete search history.

(56) References Cited

U.S. PATENT DOCUMENTS

| 4,270,525 A | 6/1981 | Furihata |
| 4,526,622 A | 7/1985 | Takamura et al. |
| (Continued) | | |

FOREIGN PATENT DOCUMENTS

| CN | 101301191 | 11/2008 |
| CN | 102046064 | 5/2011 |
| (Continued) | | |

OTHER PUBLICATIONS

Notice of Grounds of Rejection Dated Sep. 5, 2018 From the Japan Patent Office Re. Application No. 2016-528831. (6 Pages).
(Continued)

*Primary Examiner* — Ryan N Henderson

(57) ABSTRACT

A sleeve assembly is described for coupling a colonoscope insertion tube to an add-on tube. In some embodiments, the sleeve assembly defines an elongated lumen and comprises an inner sleeve sized to receive an insertion tube of a colonoscope, an outer sleeve encircling the inner sleeve, and one or more add-on tubes positioned between the inner sleeve and the outer sleeve. In some embodiments, at least the inner sleeve is collapsible to fit tightly over a colonoscope insertion tube received within the inner sleeve. In some embodiments, the inner sleeve is coupled to the outer sleeve at one or more locations along the length of the inner sleeve so that collapsing of the inner sleeve brings the outer sleeve radially closer to the inner sleeve, approximating the one or more add-on tubes to a colonoscope insertion tube received within the inner sleeve.

21 Claims, 13 Drawing Sheets

Related U.S. Application Data 2015, now Pat. No. 9,949,618, which is a continuation-in-part of application No. 14/722,400, filed on May 27, 2015, which is a continuation-in-part of application No. PCT/IL2014/051014, filed on Nov. 20, 2014.

(60) Provisional application No. 62/012,997, filed on Jun. 17, 2014, provisional application No. 61/906,982, filed on Nov. 21, 2013.

(51) Int. Cl.
  *A61B 1/018* (2006.01)
  *A61B 1/015* (2006.01)

(52) U.S. Cl.
  CPC ...... *A61B 1/00094* (2013.01); *A61B 1/00112* (2013.01); *A61B 1/00119* (2013.01); *A61B 1/00121* (2013.01); *A61B 1/00128* (2013.01); *A61B 1/00142* (2013.01); *A61B 1/015* (2013.01); *A61B 1/018* (2013.01); *A61B 1/31* (2013.01)

(56) References Cited

U.S. PATENT DOCUMENTS

| | | | |
|---|---|---|---|
| 5,096,385 A | 3/1992 | Georgi et al. | |
| 5,201,908 A | 4/1993 | Jones | |
| 5,279,542 A | 1/1994 | Wilk | |
| 5,545,121 A * | 8/1996 | Yabe | A61B 1/00142 206/363 |
| 5,554,098 A | 9/1996 | Yabe et al. | |
| 5,630,795 A | 5/1997 | Kuramoto et al. | |
| 5,674,182 A | 10/1997 | Suzuki et al. | |
| 5,679,110 A | 10/1997 | Hamazaki | |
| 5,725,476 A | 3/1998 | Yasui et al. | |
| 5,725,477 A | 3/1998 | Yasui et al. | |
| 5,788,650 A | 8/1998 | Dotolo | |
| 5,924,977 A * | 7/1999 | Yabe | A61B 1/00137 600/121 |
| 6,309,346 B1 | 10/2001 | Farhadi | |
| 6,409,657 B1 | 6/2002 | Kawano | |
| 6,641,553 B1 | 11/2003 | Chee et al. | |
| 6,786,864 B2 | 9/2004 | Matsuura et al. | |
| D536,449 S | 2/2007 | Nakajima et al. | |
| 2001/0053909 A1 | 12/2001 | Nakada et al. | |
| 2004/0127891 A1 * | 7/2004 | Humble | A61B 1/00142 606/1 |
| 2005/0033264 A1 | 2/2005 | Redinger | |
| 2005/0154262 A1 | 7/2005 | Banik et al. | |
| 2005/0256464 A1 | 11/2005 | Pallas | |
| 2006/0025729 A1 | 2/2006 | Leiboff et al. | |
| 2006/0069304 A1 | 3/2006 | Takemoto et al. | |
| 2006/0079861 A1 | 4/2006 | Matasov | |
| 2006/0235458 A1 | 10/2006 | Belson | |
| 2006/0270906 A1 | 11/2006 | Matsuno | |
| 2007/0015965 A1 | 1/2007 | Cox et al. | |
| 2007/0234716 A1 | 10/2007 | Hirooka | |
| 2008/0188715 A1 | 8/2008 | Fujimoto | |
| 2009/0143722 A1 | 6/2009 | Kim | |
| 2009/0198212 A1 | 8/2009 | Timberlake et al. | |
| 2009/0292172 A1 | 11/2009 | Roskopf et al. | |
| 2010/0025644 A1 | 2/2010 | Jockisch | |
| 2010/0063358 A1 | 3/2010 | Kessler | |
| 2010/0076420 A1 | 3/2010 | Carter | |
| 2010/0185056 A1 | 7/2010 | Gordon et al. | |
| 2010/0185150 A1 | 7/2010 | Zacharias | |
| 2010/0256447 A1 | 10/2010 | Dubi et al. | |
| 2010/0298773 A1 | 11/2010 | Nitsan et al. | |
| 2011/0034865 A1 | 2/2011 | Wallace | |
| 2011/0092892 A1 | 4/2011 | Nitsan et al. | |
| 2011/0105845 A1 | 5/2011 | Gordon et al. | |
| 2012/0101336 A1 | 4/2012 | Hirsch et al. | |
| 2012/0289910 A1 | 11/2012 | Shtul et al. | |
| 2013/0046138 A1 | 2/2013 | McLawhorn | |
| 2013/0085442 A1 | 4/2013 | Shtul et al. | |
| 2013/0131453 A1 | 5/2013 | Imai | |
| 2013/0296771 A1 | 11/2013 | Shtul et al. | |
| 2013/0331855 A1 | 12/2013 | Smith et al. | |
| 2015/0257633 A1 | 9/2015 | Hassidov et al. | |
| 2016/0206805 A1 | 7/2016 | Hassidov et al. | |
| 2016/0317000 A1 | 11/2016 | Hassidov et al. | |
| 2016/0324412 A1 | 11/2016 | Hassidov et al. | |
| 2017/0173256 A1 | 6/2017 | Hassidov et al. | |
| 2018/0020905 A1 | 1/2018 | Chouinard et al. | |
| 2019/0247566 A1 | 8/2019 | Hassidov et al. | |
| 2019/0298910 A1 | 10/2019 | Hassidov et al. | |

FOREIGN PATENT DOCUMENTS

| | | |
|---|---|---|
| CN | 102076271 | 5/2011 |
| CN | 102137615 | 7/2011 |
| CN | 102711590 | 10/2012 |
| CN | 102892445 | 1/2013 |
| DE | 3624428 | 1/1988 |
| EP | 1284120 | 2/2003 |
| EP | 1508294 | 2/2005 |
| EP | 2417896 | 2/2012 |
| JP | 50-81088 | 11/1973 |
| JP | 59-183202 | 12/1984 |
| JP | 05-161711 | 6/1993 |
| JP | 06-237887 | 8/1994 |
| JP | 06-066605 | 9/1994 |
| JP | 07-136103 | 5/1995 |
| JP | 07-155283 | 6/1995 |
| JP | 07-178040 | 7/1995 |
| JP | 11-216104 | 8/1999 |
| JP | 11-335405 | 12/1999 |
| JP | 2000-014767 | 1/2000 |
| JP | 2001-061760 | 3/2001 |
| JP | 2003-265595 | 9/2003 |
| JP | 2004-008822 | 1/2004 |
| JP | 2004-129951 | 4/2004 |
| JP | 2004-357846 | 12/2004 |
| JP | 2005-095582 | 4/2005 |
| JP | 2005-137423 | 6/2005 |
| JP | 2006-325816 | 12/2006 |
| JP | 2007-278191 | 10/2007 |
| JP | 2007-536073 | 12/2007 |
| JP | 2008-532727 | 8/2008 |
| JP | 2008-206559 | 9/2008 |
| JP | 2011-083329 | 4/2011 |
| JP | 2011-518584 | 6/2011 |
| JP | 2011-520567 | 7/2011 |
| JP | 2013-516300 | 5/2013 |
| JP | 2013-532023 | 8/2013 |
| JP | 2014-018563 | 2/2014 |
| JP | WO 2012/141261 | 7/2014 |
| WO | WO 92/17219 | 10/1992 |
| WO | WO 99/60934 | 12/1999 |
| WO | WO 00/54653 | 9/2000 |
| WO | WO 01/12102 | 2/2001 |
| WO | WO 2005/110580 | 11/2005 |
| WO | WO 2005/117685 | 12/2005 |
| WO | WO 2006/039511 | 4/2006 |
| WO | WO 2006/101908 | 9/2006 |
| WO | WO 2008/093288 | 8/2008 |
| WO | WO 2008/155776 | 12/2008 |
| WO | WO 2009/040744 | 4/2009 |
| WO | WO 2009/095915 | 8/2009 |
| WO | WO 2009/125387 | 10/2009 |
| WO | WO 2009/143201 | 11/2009 |
| WO | WO 2010/138521 | 12/2010 |
| WO | WO 2011/083450 | 7/2011 |
| WO | WO 2011/083451 | 7/2011 |
| WO | WO 2011/158232 | 12/2011 |
| WO | WO 2015/029039 | 3/2015 |
| WO | WO 2015/075721 | 5/2015 |
| WO | WO 2015/155776 | 10/2015 |
| WO | WO 2015/193896 | 12/2015 |
| WO | WO 2016/189533 | 12/2016 |
| WO | WO 2020/035868 | 2/2020 |

(56) References Cited

FOREIGN PATENT DOCUMENTS

OTHER PUBLICATIONS

Translation Dated Sep. 20, 2018 of Notice of Grounds of Rejection Dated Sep. 5, 2018 From the Japan Patent Office Re. Application No. 2016-528831. (7 Pages).
Notice of Allowance dated Dec. 5, 2018 From the U.S. Patent and Trademark Office Re. U.S. Appl. No. 14/915,266. (18 pages).
Notice of Grounds of Rejection dated Nov. 6, 2018 From the Japan Patent Office Re. U.S. Appl. No. 2017-227752. (2 Pages).
Translation dated Nov. 14, 2018 of Notice of Grounds of Rejection dated Nov. 6, 2018 From the Japan Patent Office Re. Application No. 2017-227752. (2 Pages).
Communication Pursuant to Article 94(3) EPC dated Apr. 4, 2018 From the European Patent Office Re. Application No. 14816424.7. (5 Pages).
Notice of Reasons for Rejection dated Jul. 10, 2018 From the Japan Patent Office Re. Application No. 2016-537600 and Its Summary in English. (9 Pages).
Applicant-Initiated Interview Summary dated Aug. 4, 2017 From the U.S. Patent and Trademark Office Re. U.S. Appl. No. 14/722,400. (3 Pages).
Applicant-Initiated Interview Summary dated Sep. 14, 2017 From the U.S. Patent and Trademark Office Re. U.S. Appl. No. 15/108,601. (3 pages).
Communication Pursuant to Article 94(3) EPC dated Jan. 3, 2017 From the European Patent Office Re. Application No. 15735746.8. (4 Pages).
Communication Relating to the Results of the Partial International Search dated Feb. 24, 2015 From the International Searching Authority Re. Application No. PCT/IL2014/051014.
International Preliminary Report on Patentability dated Jun. 2, 2016 From the International Bureau of WIPO Re. Application No. PCT/IL2014/051014.
International Preliminary Report on Patentability dated Dec. 7, 2017 From the International Bureau of WIPO Re. Application No. PCT/IL2016/050544. (8 Pages).
International Preliminary Report on Patentability dated Mar. 10 2016 From the International Bureau of WIPO Re. Application No. PCT/IL2014/050778.
International Preliminary Report on Patentability dated Oct. 20, 2016 From the International Bureau of WIPO Re. Application No. PCT/IL2015/050379. (9 Pages).
International Preliminary Report on Patentability Dated Dec. 29, 2016 From the International Bureau of WIPO Re. Application No. PCT/IL2015/050615. (8 Pages).
International Search Report and the Written Opinion dated May 6, 2015 From the International Searching Authority Re. Application No. PCT/IL2014/051014.
International Search Report and the Written Opinion dated Dec. 8, 2014 From the International Searching Authority Re. Application No. PCT/IL2014/050778.
International Search Report and the Written Opinion dated Sep. 11, 2016 From the International Searching Authority Re. Application No. PCT/IL2016/050544.
International Search Report and the Written Opinion dated Oct. 13, 2015 From the International Searching Authority Re. Application No. PCT/IL2015/050615.
International Search Report and the Written Opinion dated Feb. 16, 2016 From the International Searching Authority Re. Application No. PCT/IL2015/050379.
International Search Report and the Written Opinion dated Oct. 16, 2015 From the International Searching Authority Re. Application No. PCT/IL2015/050379.
Invitation to Pay Additional Fees dated Aug. 12, 2015 From the International Searching Authority Re. Application No. PCT/IL2015/050379.
Notice of Grounds of Rejection dated Jun. 27, 2017 From the Japan Patent Office Re. Application No. 2016-553662. (3 Pages).
Notice of Grounds of Rejection dated Jan. 31, 2017 From the Japan Patent Office Re. Application No. 2016-553662. (3 Pages).
Notification of Office Action and Search Report dated Nov. 16, 2017 From the State Intellectual Property Office of the People's Republic of China Re. Application No. 201580037467.6. (9 Pages).
Official Action dated Apr. 5, 2018 From the U.S. Patent and Trademark Office Re. U.S. Appl. No. 14/915,266. (62 pages).
Official Action dated Apr. 6, 2018 From the U.S. Patent and Trademark Office Re. U.S. Appl. No. 15/301,968. (52 pages).
Official Action dated Jun. 6, 2017 from the U.S. Patent and Trademark Office Re. U.S. Appl. No. 14/722,400. (51 pages).
Official Action Dated Nov. 8, 2017 From the U.S. Patent and Trademark Office Re. U.S. Appl. No. 14/722,400. (23 pages).
Official Action dated Oct. 19, 2017 From the U.S. Patent and Trademark Office Re. U.S. Appl. No. 15/108,601. (38 pages).
Official Action dated May 31, 2017 From the U.S. Patent and Trademark Office Re. U.S. Appl. No. 15/108,601. (46 Pages).
Restriction Official Action dated Jan. 16, 2018 From the U.S. Patent and Trademark Office Re. U.S. Appl. No. 14/915,266. (8 pages).
Restriction Official Action dated Nov. 16, 2016 From the U.S. Patent and Trademark Office Re. U.S. Appl. No. 14/722,400. (11 pages).
Restriction Official Action dated Feb. 28, 2017 From the US Patent and Trademark Office Re. U.S. Appl. No. 14/722,400. (11 pages.
Restriction Official Action dated Mar. 29, 2017 From the US Patent and Trademark Office Re. U.S. Appl. No. 15/108,601. (10 Pages).
Supplementary European Search Report and the European Search Opinion dated Dec. 1, 2017 From the European Patent Office Re. Application No. 15776016.6. (10 Pages).
Translation of Notice of Grounds of Rejection dated Jun. 27, 2017 From the Japan Patent Office Re. Application No. 2016-553662. (3 Pages).
Translation of Notice of Grounds of Rejection dated Jan. 31, 2017 From the Japan Patent Office Re. Application No. 2016-553662. (4 Pages).
Translation of Notification of Office Action dated Nov. 16, 2017 From the State Intellectual Property Office of the People's Republic of China Re. Application No. 201580037467.6. (2 Pages).
Ambrose et al. "Physiological Consequences of Orthograde Lavage Bowel Preparation for Elective Colorectal Surgery: A Review", Journal of the Royal Society of Medicine,76(9): 767-771, Sep. 1983. p. 768, 2nd Paragraph.
European Search Report and the European Search Opinion dated Mar. 23, 2018 From the European Patent Office Re. Application No. 17196947.0. (7 Pages).
Translation dated Jul. 24, 2018 of Notice of Reasons for Rejection dated Jul. 10, 2018 From the Japan Patent Office Re. Application No. 2016-537600 and Its Summary in English. (9 Pages).
Notice of Reasons for Rejection dated Feb. 6, 2019 From the Japan Patent Office Re. Application No. 2016-559518 and Its Translation Into English. (12 Pages).
Translation Dated Jul. 18, 2019 of Notification of Reasons for Refusal dated Jun. 25, 2019 From the Japan Patent Office Re. Application No. 2016-537600. (7 Pages).
Notice of Reasons for Rejection dated Jun. 25, 2019 From the Japan Patent Office Re. Application No. 2016-537600 and Its Summary in English. (8 Pages).
Supplementary European Search Report and the European Search Opinion dated Mar. 21, 2019 From the European Patent Office Re. Application No. 16799477.1. (10 Pages).
Notification of Office Action and Search Report dated Apr. 1, 2019 From the State Intellectual Property Office of the People's Republic of China Re. Application No. 201680002365.5 and Its Summary in English. (9 Pages).
Official Action dated Mar. 15, 2019 From the U.S. Patent and Trademark Office Re. U.S. Appl. No. 14/722,400. (41 pages).
Translation dated Apr. 9, 2019 of Notification of Office Action dated Apr. 1, 2019 From the State Intellectual Property Office of the People's Republic of China Re. Application No. 201680002365.5. (5 Pages).

(56) References Cited

OTHER PUBLICATIONS

Notification of Office Action and Search Report dated Jun. 3, 2020 From the State Intellectual Property Office of the People's Republic of China Re. Application No. 201680002365.5 and Its Summary in English. (7 Pages).
Notification of Reason for Refusal dated May 19, 2020 From the Japan Patent Office Re. Application No. 2016-537600 and Its Translation Into English. (10 Pages).
Translation dated Jun. 9, 2020 of Notification of Office Action dated Jun. 3, 2020 From the State Intellectual Property Office of the People's Republic of China Re. Application No. 201680002365.5. (2 Pages).
Communication Pursuant to Article 94(3) EPC dated May 8, 2020 From the European Patent Office Re. Application No. 14816424.7. (4 Pages).
Notification of Office Action dated Dec. 16, 2019 From the State Intellectual Property Office of the People's Republic of China Re. Application No. 201680002365.5. (4 Pages).
Notification of Office Action and Search Report dated Apr. 16, 2020 From the State Intellectual Property Office of the People's Republic of China Re. Application No. 201810576718.3 and Its Translation of Office Action Into English. (14 Pages).
Decision to Grant dated Jan. 6, 2020 From the Japan Patent Office Re. Application No. 2016-559518. (3 Pages).
International Search Report and the Written Opinion dated Dec. 26, 2019 From the International Searching Authority Re. Application No. PCT/IL2019/050919. (12 Pages).
Decision to Grant Patent dated Jul. 16, 2019 From the Japan Patent Office Re. Application No. 2017-227752 and Its Translation Into English. (6 Pages).
Translation dated Dec. 30, 2019 of Notification of Office Action dated Dec. 16, 2019 From the State Intellectual Property Office of the People's Republic of China Re. Application No. 201680002365.5. (2 Pages).
Communication Pursuant to Article 94(3) EPC dated Nov. 11, 2019 From the European Patent Office Re. Application No. 14771962.9. (5 Pages).
Official Action dated Oct. 2, 2019 From the U.S. Patent and Trademark Office Re. U.S. Appl. No. 14/722,400. (28 pages).
Communication Pursuant to Article 94(3) EPC dated Jun. 5, 2020 From the European Patent Office Re. Application No. 17196947.0. (5 Pages).
Notice of Reasons for Rejection dated Jun. 16, 2020 From the Japan Patent Office Re. Application No. 2017-559659 and Its Translation Into English. (9 Pages).
Notice of Allowance dated Oct. 1, 2020 from the U.S. Patent and Trademark Office Re. U.S. Appl. No. 14/722,400. (26 pages).
Decision of Refusal dated Sep. 1, 2020 From the Japan Patent Office Re. Application No. 2016-537600 and Its Translation Into English. (10 Pages).
Notification of Office Action and Search Report dated Sep. 23, 2020 From the State Intellectual Property Office of the People's Republic of China Re. Application No. 201810576718.3 and Its Translation of Office Action Into English. (8 Pages).

\* cited by examiner

APPARATUS AND METHOD FOR COUPLING BETWEEN A COLONOSCOPE AND ADD-ON TUBES

RELATED APPLICATIONS

This application is a divisional of patent application Ser. No. 15/108,601 filed on Jun. 28, 2016 which is a National Phase of PCT Patent Application No. PCT/IL2015/050615 having International filing date of Jun. 17, 2015, which claims the benefit of priority under 35 USC § 119(e) of U.S. Provisional Patent Application No. 62/012,997 filed on Jun. 17, 2014.

PCT Patent Application No. PCT/IL2015/050615 is also a Continuation-in-Part (CIP) of U.S. patent application Ser. No. 14/722,400 filed on May 27, 2015, which is a Continuation-in-Part (CIP) of PCT Patent Application No. PCT/IL2014/051014 having International filing date of Nov. 20, 2014, which claims the benefit of priority under 35 USC § 119(e) of U.S. Provisional Patent Application Nos. 62/012,997 filed on Jun. 17, 2014 and 61/906,982 filed on Nov. 21, 2013.

The contents of the above applications are all incorporated by reference as if fully set forth herein in their entirety.

FIELD AND BACKGROUND OF THE INVENTION

The present invention, in some embodiments thereof, relates to a colon cleaning system, and more particularly, but not exclusively, to a device and method for coupling between a colonoscope and one or more add-on tubes.

U.S Publication No. 2012/0101336 A1 to Hirsch et al. discloses "An endoscopic system for use with an endoscope, including an irrigation tube that provides a flow of irrigation fluid for cleaning a body lumen, and a suction tube for sucking material from the body lumen, wherein the suction tube is connected to a branch connector and one branch of the branch connector is connected to a suction source tube which is connected to a suction source and another branch of the branch connector is connected to a vent tube, and wherein the suction source tube and the vent tube pass through a double pinch valve."

SUMMARY OF THE INVENTION

According to an aspect of some embodiments, there is provided a sleeve assembly for coupling between a colonoscope insertion tube and one or more add-on tubes, the sleeve assembly comprising: an inner sleeve defining an elongated lumen with an open end, and an having an expanded state sized to surroundingly receive at least 70% of the length of the colonoscope insertion tube arranged longitudinally within the inner sleeve; an outer sleeve encircling the inner sleeve; and one or more add-on tubes extending longitudinally between the inner sleeve and the outer sleeve; wherein inner sleeve is collapsible from the expanded state to fit tightly over the received length of colonoscope insertion tube; and wherein the inner sleeve is coupled to the outer sleeve at one or more locations along the inner sleeve so that collapsing the inner sleeve from the expanded state brings the outer sleeve radially closer to the inner sleeve, approximating the one or more add-on tubes to the inner sleeve.

According to some embodiments, at least one of the outer sleeve and the inner sleeve is radially stretched in the expanded state, and sufficiently elastic to drive the collapse to the tight fit over the received length of colonoscope insertion tube.

According to some embodiments, the radial stretch in the expanded state comprises stretching which increases the diameter of the inner sleeve by at least 2 mm over an unstretched state of the elastic sleeve.

According to some embodiments, the unstretched state of the elastic sleeve has a diameter of less than 12 mm.

According to some embodiments, in the expanded state of the inner sleeve, a diameter of the inner sleeve is at least 10% larger than a diameter of the colonoscope insertion tube receivable within the inner sleeve.

According to some embodiments, in a relaxed collapsed state of the inner sleeve a diameter of the inner sleeve is at least 5% smaller than a diameter of a selected diameter of colonoscope insertion tube received within it, to tightly fit the insertion tube.

According to some embodiments, the inner sleeve is expandable in a radially outwards direction along at least 60% of the length of the inner sleeve.

According to some embodiments, the inner sleeve is expandable along its complete length.

According to some embodiments, the outer sleeve is expanded as a result of expansion of the inner sleeve.

According to some embodiments, an inner circumferential surface of the outer sleeve is attached to an outer circumferential surface of the inner sleeve in at least one region along the sleeves.

According to some embodiments, the stiffness at least the inner sleeve varies along the longitudinal extent of the elongated lumen of the inner sleeve.

According to some embodiments, at least one of the add-on tubes is suitable for irrigation of the colon, and at least one of the add-on tubes is suitable for evacuation of matter from the colon.

According to some embodiments, at least one of the add-on tubes comprises a sensor.

According to some embodiments, the sensor is a pressure sensor.

According to some embodiments, the outer sleeve is shaped as a continuous cylinder having a length at least as long as a colonoscope insertion tube received within the inner sleeve.

According to some embodiments, at least one of the inner sleeve and the outer sleeve is non-contiguous and is formed of a plurality of elements interconnected by an axially extending element.

According to some embodiments, the elements are one or more collinear sleeves.

According to some embodiments, a length of the inner sleeve is in a range between 80 and 165 cm.

According to some embodiments, the outer sleeve comprises at least one guide member shaped to align the add-on tubes with respect to a longitudinal axis of the inner sleeve, thereby aligning the add-on tubes with respect to a colonoscope insertion tube received within the sleeve.

According to some embodiments, an inner surface of the outer sleeve defines one or more elongated grooves for receiving the one or more add-on tubes, the grooves extending parallel to a longitudinal axis of the inner sleeve in which a colonoscope insertion tube is received or at an angle with respect to the longitudinal axis of the inner sleeve.

According to some embodiments, the sleeve assembly comprises polyurethane.

According to some embodiments, the sleeve assembly further comprises an external sleeve encircling the outer sleeve to prevent over expansion during set up of a colonoscope insertion tube and add-on tubes using the sleeve assembly.

According to some embodiments, at least a portion of the inner and outer sleeves is defines a viewing window to enable viewing scale marks on a colonoscope insertion tube.

According to some embodiments, at least a distal end of the sleeve assembly is flexible to increase compliance with tissue when the sleeve assembly is used within a colon.

According to some embodiments, migration of the add-on tubes with respect to the colonoscope insertion tube is prevented along at least 60% of the length of the sleeve assembly when the add-on tubes are approximated to the inner sleeve.

According to some embodiments, the outer sleeve comprises a first outer layer adapted for contacting the walls of a colon when the sleeve is inserted to the colon, and a second inner layer holding the add-on tubes to the inner sleeve; the outer layer comprising a material having a friction coefficient smaller than a friction coefficient of a material of the inner layer.

According to some embodiments, the coupling of the outer sleeve to the inner sleeve comprises mutual attachment extending longitudinally along at least 50% of the length of the sleeve assembly.

According to an aspect of some embodiments of the invention, there is provided a system for coupling between a colonoscope insertion tube and one or more add-on tubes, comprising: a sleeve assembly; and an inflation module connectable to the sleeve assembly, the inflation module is configured to inflate at least a portion of the sleeve assembly to expand it.

According to some embodiments, the inflation module comprises an air pump and a regulator.

According to some embodiments, a proximal end of the sleeve assembly comprises a housing structured to couple between the sleeve assembly and the inflation module, the housing comprising a valve.

According to some embodiments, the housing is connected to a knob, the knob movable for selecting an orientation of the add-on tubes with respect to a handle of a colonoscope when an insertion tube of the colonoscope is positioned within the inner sleeve.

According to some embodiments, the system further comprises a jig shaped to receive at least a portion of the sleeve assembly.

According to some embodiments, the jig comprises one or more sensors for detecting at least one of a lengthwise positioning of a colonoscope insertion tube with respect to the sleeve assembly, and a positioning of the add-on tubes with respect to the colonoscope insertion tube.

According to some embodiments, the jig is serves as a packaging of the sleeve assembly.

According to some embodiments, the jig is telescopic and is expandable to at least a length of a colonoscope insertion tube received within the inner sleeve.

According to an aspect of some embodiments, there is provided a method for coupling between a colonoscope insertion tube and one or more add-on tubes, comprising: providing a sleeve assembly having at least one lumenal wall defining a longitudinally extending lumen and including at least one add-on tube also passing along the longitudinal extent of the sleeve assembly; positioning a colonoscope insertion tube in the longitudinally extending lumen; collapsing the sleeve assembly so that the add-on tubes are approximated radially closer to the colonoscope insertion tube, the sleeve assembly maintaining the add-on tubes in the approximated position with respect to the colonoscope insertion tube.

According to some embodiments, the method further comprises expanding an inner diameter of at least a portion of the sleeve before positioning the colonoscope insertion tube.

According to some embodiments, the expanding comprises inflating the sleeve.

According to some embodiments, the inflating comprises inflating with at least one of air and liquid.

According to some embodiments, the sleeve assembly comprises an inner sleeve surrounded by an outer sleeve, and wherein the expanding comprises reducing a volume of a lumen defined between outer walls of the inner sleeve and inner walls of the outer sleeve.

According to some embodiments, the reducing a volume comprises removing material from the lumen.

According to some embodiments, the removing comprises suctioning air out of the lumen.

According to some embodiments, the inner sleeve is expanded to a diameter larger than a diameter of the colonoscope insertion tube to reduce friction between the colonoscope insertion tube and walls of the inner sleeve during the positioning of the colonoscope insertion tube in the inner sleeve.

According to some embodiments, the expanding comprises stretching the sleeve along the longitudinal extent, and the collapsing is such that longitudinal tension remains in the at least one lumenal wall of the sleeve assembly after the add-on-tubes are approximated.

According to some embodiments, the collapsing fixates a positioning of the add-on tubes relative to the colonoscope insertion tube.

According to some embodiments, the method further comprises orienting the add-on tubes with respect to the inner sleeve during the collapsing.

According to some embodiments, the method further comprises removing the colonoscope insertion tube from the sleeve assembly by pulling on a thread which extends along the sleeve assembly and protrudes from a distal or proximal end of the sleeve assembly, to tear open the sleeve.

According to some embodiments, the method further comprises threading the one or more add-on tubes to extend longitudinally within a lumen defined by the sleeve assembly.

According to some embodiments, the one or more add-on tubes are integrated in the sleeve assembly.

According to some embodiments, the collapsing comprises bringing the add-on tubes radially closer to the colonoscope insertion tube.

According to some embodiments, the positioning comprises reducing friction between the colonoscope insertion tube and the sleeve assembly by at least one of: lubricating an inner surface of the sleeve assembly which defines a lumen in which the colonoscope insertion tube is received, lubricating the colonoscope insertion tube, and coating the inner surface of the sleeve assembly with a polymer based material suitable for reducing friction.

According to an aspect of some embodiments, there is provided an apparatus for coupling between a colonoscope insertion tube and one or more add-on tubes, the apparatus comprising: a sleeve defining an elongated lumen with an open end, and an expanded state sized to surroundingly receive at least 70% of the length of the colonoscope insertion tube arranged longitudinally within the sleeve; and one or more add-on tubes coupled to the sleeve across or more extensions distributed circumferentially around the sleeve; wherein an add-on tube coupled to the sleeve by one of the extensions extends alongside the sleeve for at least 70% of a length of the sleeve.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
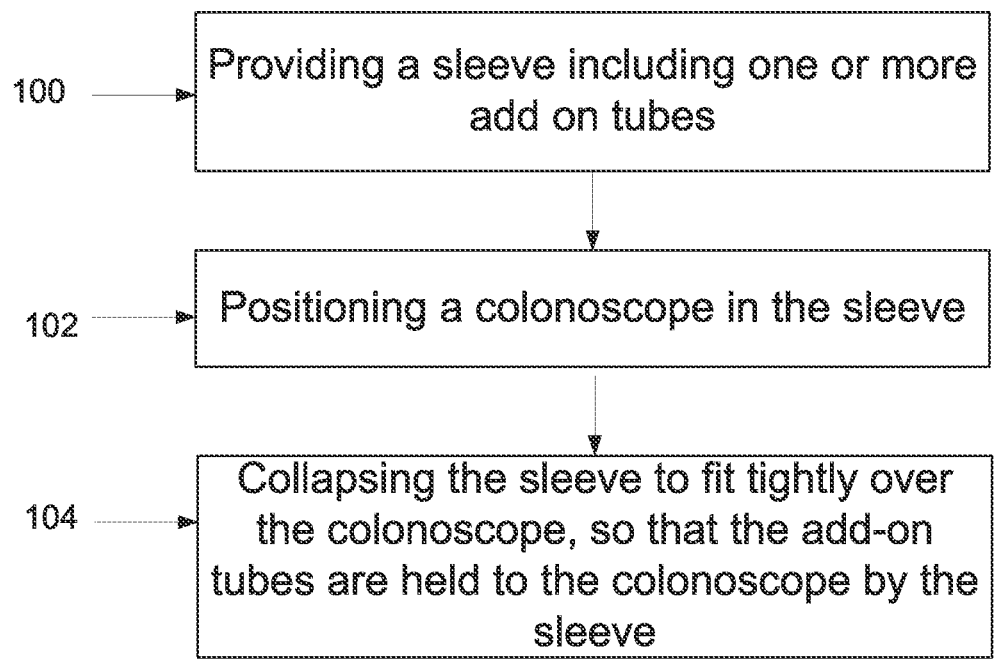
FIG. 1 is a flowchart of a general method for coupling between a colonoscope and one or more add-on tubes, according to some embodiments of the invention.

The present invention, in some embodiments thereof, relates to a colon cleaning system, and more particularly, but not exclusively, to a device and method for coupling between a colonoscope and one or more add-on tubes, configured for insertion into the colon. Optionally, a coupling is formed between an insertion tube of a colonoscope, and at least a portion of the length of one or more add-on tubes. In some embodiments, the add-on tubes comprise tubes for irrigation of the colon, tubes for evacuation of matter from the colon, and/or tubes configured for sensing within the colon, such as sensing of pressure. In some embodiments, the one or more add-on tubes and colonoscope are configured to be maneuvered together within a colon.

An aspect of some embodiments relates to coupling between a colonoscope and one or more add-on tubes. Optionally, the colonoscope is coupled to the add-on tubes outside the body, and the add-on tubes are held to the colonoscope for example by a sleeve as described herein, so that the colonoscope and tubes can be moved together.

In some embodiments, a system for coupling between the colonoscope and add-on tubes comprises a collapsible sleeve, which, when collapsed to a relaxed state, is configured to fit tightly over the colonoscope and to hold the add-on tubes to the colonoscope. In some embodiments, collapsing of the sleeve brings the one or more add-on tubes radially closer to the colonoscope. Optionally, the collapsed sleeve attaches between the colonoscope and tubes along at least a portion of the colonoscope, for example along a total of 60%, 70%, 80% or intermediate, larger or smaller percentages of the colonoscope's length. Optionally, the tubes and the colonoscope are attached at a plurality of spaced apart segments.

In some embodiments, collapsing of the sleeve comprises removing air from the sleeve. Optionally, not all parts of the sleeve are collapsed at the same time, for example a distal end of the sleeve is collapsed before a proximal end. Alternatively, the sleeve is collapsed at once. Optionally, the sleeve is collapsed by removal of a cap, for example from a distal end of the sleeve, thus enabling air to flow out of the sleeve.

In some embodiments, air bubbles which may form, for example, between the colonoscope and the sleeve are removed, for example by applying vacuum following the collapsing.

In some embodiments, in a non-collapsed state of the sleeve, a diameter of the sleeve is at least 5%, 10%, 20% or intermediate, larger or smaller percentages larger than a diameter of a colonoscope intended to be positioned within the sleeve.

Optionally, in a non-collapsed state of the sleeve, the sleeve is expanded in a radially outwards direction, for example by inflation. A potential advantage of an expanded sleeve may include facilitating insertion of the colonoscope into the sleeve during set up, for example by threading the colonoscope into the sleeve.

In some embodiments, the sleeve is a cylinder comprising one or more internal lumens. Optionally, the one or more lumens extend between a proximal end and a distal end of the sleeve. In some embodiments, the sleeve extends to a length at least as long as a colonoscope received within it. Optionally, the sleeve is continuous.

Alternatively, the sleeve is non-continuous, and is formed of, for example, a plurality of tubular segments or rings.

Optionally, the sleeve is configured for aligning between the colonoscope and the add-on tubes, for example aligning the add-on tubes with respect to a longitudinal axis of the colonoscope. In some embodiments, the sleeve is shaped to hold the tubes wound around the colonoscope. Additionally or alternatively, the sleeve holds the tubes aligned in parallel to the colonoscope. In some embodiments, the shaping of the sleeve for tube alignment comprises providing the sleeve with one or more guide members; for example, a closed channel, a guide-wall, and/or another form of longitudinally extending (optionally, helical or partially helical) protrusion and/or groove which provides a track along which a tube is constrained to extend.

In some embodiments, a coupling between the colonoscope and add-on tubes is formed with some degree of freedom, for example allowing, to a certain extent, axial sliding of the add-on tubes with respect to the colonoscope or vice versa, allowing, to a certain extent, angular rotation of the tubes with respect to the colonoscope and/or allowing, to a certain extent and for no more than, for example, 30% of the colonoscope's length, a radial gap between the colonoscope and add-on tubes. A potential advantage of a coupling with a certain degree of freedom may include reducing a rigidity of the complete colonoscope and add-on tubes assembly, which may facilitate maneuvering in the colon. In some embodiments, a rigidity is reduced by using the sleeve to couple between the colonoscope and add-on tubes along only a portion of the colonoscope's length, for example along 40%, 60%, 85% or intermediate, larger or smaller percentages of the length, and using other coupling means to couple the rest of the colonoscope's length to the tubes, for example using a plurality of tape wraps.

In some embodiments, a sleeve assembly is provided, for example including an inner sleeve positioned within an outer sleeve. Optionally, the inner sleeve is attached to the outer sleeve along at least a circumferential segment of the sleeves' walls. In some embodiments, the inner sleeve is configured to receive a colonoscope, and a lumen between the inner sleeve and the outer sleeve includes the add-on tubes to be coupled to the colonoscope. Optionally, the one or more add-on tubes are an integrated part of the sleeve. Additionally or alternatively, the one or more add-on tubes are passed within the lumen.

In some embodiments, expansion of the sleeve assembly or a portion of it such as the inner sleeve is obtained by inflation. Optionally, inflation is carried out by connecting the sleeve assembly, for example through a valve, to an inflation module.

Optionally, the inflation module comprises a pump and a pressure regulator. In some embodiments, the inner sleeve is inflated, and the outer sleeve, which encircles the inner sleeve, is caused to expand as well. In some embodiments, inflation causes overstretching of the inner and/or outer sleeve longitudinally, so that when collapsed, ripples are reduced. Optionally, inflation is performed to detect tears or other defects in the sleeve.

In some embodiments, the inner and/or outer sleeves are formed with varying degrees of stiffness, for example different stiffness properties for different longitudinal sections of the sleeve, to accommodate portions of the colonoscope having different flexibility properties.

In some embodiments, the add-on tubes are oriented with respect to a handle of the colonoscope, for example so that maneuvering of the colonoscope within the body is least affected by the add-on tubes.

In some embodiments, the system comprises a jig for use during set up of the sleeve and add-on tubes. Optionally, the jig is shaped to straighten the sleeve assembly during the attachment process. Optionally, the jig is shaped and/or sized to prevent overexpansion of the sleeve assembly. Optionally, the jig is shaped to define a track for threading of the colonoscope and/or the add-on tubes, so that they are positioned at a designated orientation with respect to each other.

In some embodiments, the jig is a telescopic track which can be expanded to at least a length of the colonoscope. In some embodiments, a packaging of the sleeve serves as the jig. In some embodiments, an external sleeve, for example a rigid sleeve, serves as the jig. Optionally, the rigid external sleeve reduces or prevents over expansion. In some embodiments, a colonoscope's works station is formed with a jig on which the colonoscope and add-on tubes can be set up.

In some embodiments, the jig comprises one or more sensors, for example for detecting a pressure level in the sleeve assembly, detecting a positioning of the colonoscope and/or add-on tubes, and/or detecting a fit of the collapsed sleeve assembly to the colonoscope.

Additionally or alternatively, means other than the jig are used for aligning the colonoscope and the add-on tubes, for example, a bridge shape element which is slid over the sleeve assembly to straighten it, or vertically hanging the sleeve assembly, utilizing gravity to straighten it.

In some embodiments, a disposable sleeve with pre-attached add-on tubes is provided, and a colonoscope is threaded through to be coupled to the tubes.

It is noted that in some embodiments, the apparatuses and/or methods described herein may be applied for coupling between an endoscope and one or more add-on tubes.

As used herein, the term "proximal" may include any portion of the colonoscope, add-on tubes and/or other components of the colonoscopy system which are closer to a user manipulated end of the device, and may be configured to remain outside the body; the term "distal" may include any portion of the colonoscope, add-on tubes and/or other components of the colonoscopy system which are closer to an end configured for insertion into the colon. Orientation of other components described herein may be defined with respect to the proximal and distal ends of the system.

As referred to herein, a typical colonoscope includes one or more of an insertion tube or a portion of the insertion tube, a Y-connector, an umbilical cord, a handle. As a general note, when a colonoscope is referred to in the context of coupling to one or more add-on tubes, the term "colonoscope" may refer to at least a portion of an insertion tube of the colonoscope.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Referring now to the drawings, FIG. 1 is a flowchart of a general method for coupling between a colonoscope and one or more add-on tubes, according to some embodiments of the invention.

In some embodiments, the method is performed prior to a colonoscopy procedure, for example by a physician or other medical and/or technical personnel. In some embodiments, the method is performed externally to the body, to couple between a colonoscope and one or more add-on tubes, which are intended for insertion into a patient's colon.

In some embodiments, a sleeve is provided (100). Optionally, the sleeve comprises one or more add-on tubes. Optionally, the add-on tubes are an integrated part of the sleeve, for example attached to an inner wall of the sleeve. Additionally or alternatively, one or more tubes are inserted into the sleeve. Optionally, the tubes are passed along a length of the sleeve.

In some embodiments, the add-on tubes comprise one or more of: a tube for irrigation of the colon; a tube for evacuation of matter from the colon, such as fecal matter; a tube configured for sensing within the colon, for example a tube comprising a pressure sensor at its distal end; a tube configured to deliver a tool into the colon.

Optionally, the one or more add-on tubes are connected to a work station, for example at their proximal end. For example, in some embodiments, an evacuation tube is connected to a vacuum source. In some embodiments, an irrigation tube is connected to a liquid tank. In some embodiments, a pressure sensing tube is connected a vacuum source.

In some embodiments, the sleeve is disposable. Optionally, the add-on tubes are disposable.

In some embodiments, a colonoscope is positioned within the sleeve (102).

Optionally, the colonoscope is threaded into the sleeve. Optionally, the colonoscope is rotated during insertion into the sleeve. In some embodiments, the sleeve may comprise an aperture through which the colonoscope can be placed, for example an elongated slot which can be closed once the colonoscope has been placed within the sleeve. Optionally, friction at the interface between the colonoscope and the sleeve's walls is reduced, for example to reduce the amount of force which needs to be exerted on the colonoscope to pass it through the sleeve. Optionally, friction is reduced by a sleeve having a diameter which, at least along some segments of the sleeve and/or at certain times, for example prior to collapsing of the sleeve, is larger than a diameter of the colonoscope. Optionally, an oversized diameter of the sleeve is obtained by inflating the sleeve or portions of it, for example with air. Additionally or alternatively, friction is reduced by lubricating the colonoscope and/or the inner walls of the sleeve, for example using Vaseline. Additionally or alternatively, friction is reduced by a coating on the inner walls of the sleeve which is effective to reduce friction, for example comprising a polymer material.

In some embodiments, insertion of the colonoscope into the sleeve is aided, for example, by a jig. Optionally, for example as will be further described herein, the jig defines a track for positioning of the sleeve during insertion of the colonoscope. In some embodiments, the jig straightens the sleeve, to facilitate insertion of the colonoscope through.

In some embodiments, after insertion of the colonoscope into the sleeve, the sleeve is collapsed (104). Optionally, collapsing comprises removing air from a lumen of the sleeve, for example by suctioning and/or by letting air flow out of the sleeve.

Optionally, collapsing brings the one or more add-on tubes closer to the colonoscope, for example radially closer. In some embodiments, the sleeve holds the tubes aligned parallel to a longitudinal axis of the colonoscope. Additionally or alternatively, the sleeve holds the tubes at an angle relative to a longitudinal axis of the colonoscope. Optionally, the tubes are wound around the colonoscope.

In some embodiments, the collapsed sleeve restricts movement of the add-on tubes with respect to the colonoscope or vice versa, for example radial movement inward and/or outward with respect to each other, axial movement with respect to each other, and/or rotational movement with respect to each other. Additionally or alternatively, the collapsed sleeve is arranged to provide some freedom of movement.

Optionally, the sleeve is arranged to restrict movement along some portions of the sleeve, and allow movement, for example to a certain extent, at other portions of the sleeve. For example, in some embodiments, the sleeve is arranged to allow sliding of the tubes with respect to the colonoscope. Additionally or alternatively, the sleeve is arranged to allow one or more radial gaps between the colonoscope and tubes, which may increase or decrease in size. Optionally, the radial boundary of movement is selected to maintain the complete coupled assembly of the colonoscope and tubes under a certain diameter, for example a diameter ranging between 12-25 mm, such as 14 mm, 18 mm, 24 mm or intermediate, larger or smaller diameters. A potential advantage of enabling movement of the tubes and/or colonoscope with respect to each other, for example to a certain extent, may include reducing a rigidity of the coupled assembly. Reducing a rigidity may facilitate maneuvering of the complete assembly inside the colon.

In some embodiments, for example following use, a colonoscope is removed from the sleeve. Optionally, the colonoscope is removed by cutting the sleeve.

Optionally, removing the colonoscope comprises cutting a slot, for example at a distal end of the sleeve, and tearing the sleeve open. In some embodiments, a thin thread, for example formed of metal or nylon, is previously passed within the sleeve, for example the thread is inserted along with the colonoscope, and the sleeve can be torn open by pulling on an end of the thread which extends beyond a proximal and/or distal opening of the sleeve. Optionally, the thread is integrated within the sleeve.

Figure 2:
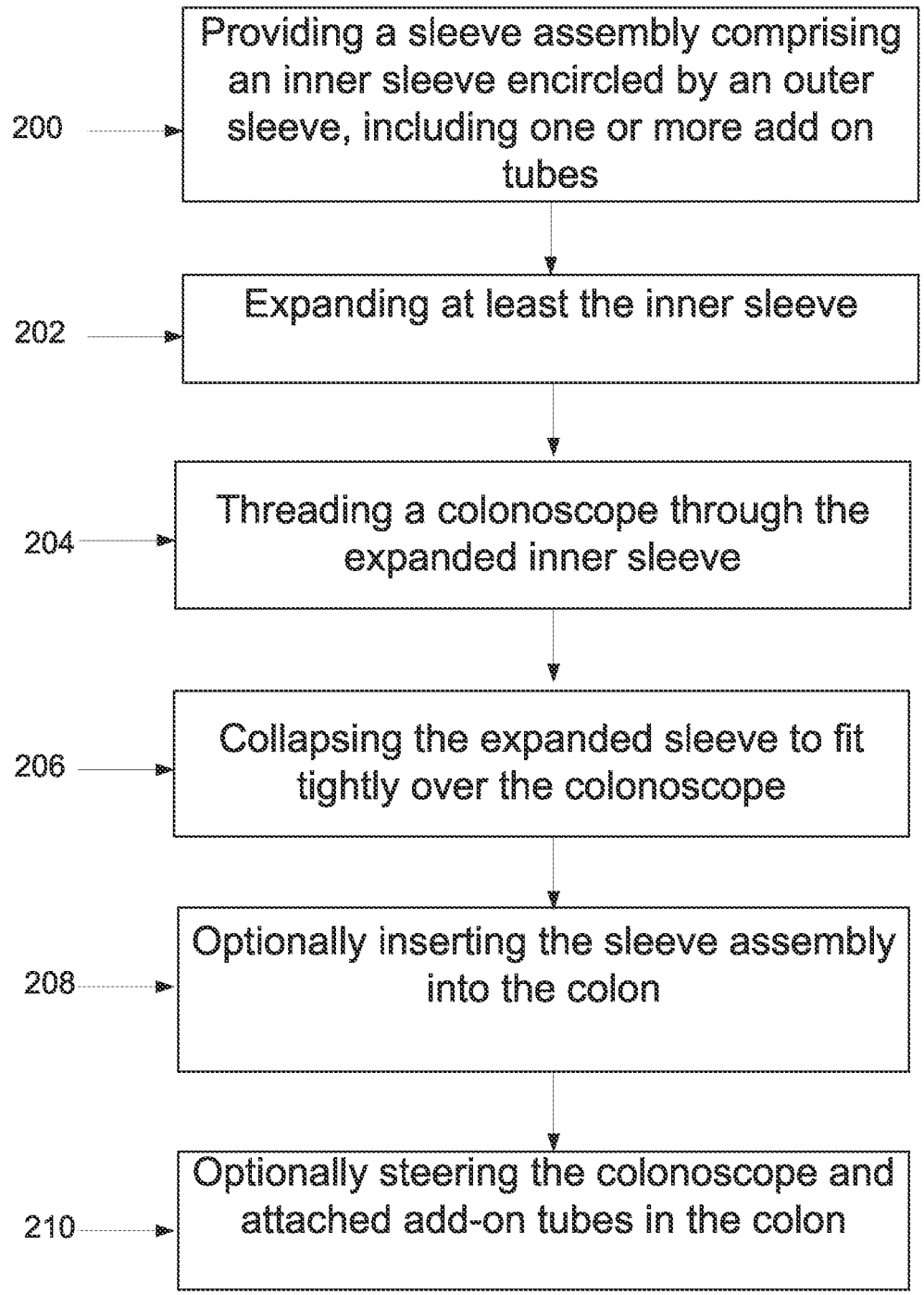
FIG. 2 is a flowchart of an exemplary method for coupling between a colonoscope and one or more add-on tubes using a sleeve assembly, according to some embodiments of the invention.

FIG. 2 is a flowchart of an exemplary method for coupling between a colonoscope and one or more add-on tubes using a sleeve assembly comprising an inner sleeve and an outer sleeve, according to some embodiments of the invention.

In some embodiments, a sleeve assembly comprising an inner sleeve encircled by an outer sleeve is provided (200). Optionally, one or more add-on tubes are an integrated part of the sleeve assembly, for example positioned at a lumen between the inner and outer sleeve. Additionally or alternatively, one or more add-on tubes are passed within the sleeve.

In some embodiments, one or more portions of the sleeve assembly are expanded. Optionally, the sleeve or one or more segments of it are expanded in a radial direction. In some embodiments, a length of the sleeve is extended in a proximal direction and/or in a distal direction.

In some embodiments, the inner sleeve is expanded (202). In some embodiments, expansion is obtained by inflating the inner sleeve, for example with air.

Additionally or alternatively, the inner sleeve is inflated with fluid. In some embodiments, the inner sleeve is expanded by removal of material, for example from a lumen between the inner and outer sleeve. Optionally, air is removed from the lumen between the sleeves, for example by suctioning, causing the inner sleeve to radially expand.

In some embodiments, the inner sleeve is expanded to a diameter similar to or larger than a diameter of a colonoscope intended to be received within the sleeve, for example 5%, 10%, 20%, 30%, or intermediate, larger or smaller percentages larger than a diameter of the colonoscope. Optionally, the walls of the inner sleeve exert force on the walls of the outer sleeve, causing it to expand as well.

In some embodiments, a material of the inner and/or outer sleeve is selected to be elastic enough to provide expansion. Alternatively, the outer sleeve is formed of a rigid material. Optionally, a rigid outer sleeve restricts the expansion of the inner sleeve.

In some embodiments, a colonoscope is inserted into the expanded inner sleeve (204), for example by threading. Optionally, the inner sleeve and/or outer sleeve are over stretched longitudinally, and may extend, for example, to a distance past a head of the colonoscope, for example extending 1 mm, 2 mm, 5 mm, 10 mm, 1 cm, 5 cm 10 cm or intermediate, larger or smaller distances past a distal head of the colonoscope. A potential advantage of over stretching may include reducing or preventing ripples and/or kinks of the sleeve, for example after collapsing.

In some embodiments, at least the inner sleeve is collapsed (206). In some embodiments, collapsing includes removing air from the sleeve, for example by suctioning the air and/or by letting air out. Optionally, the outer sleeve, due to its elastic properties, is collapsed as well. Optionally, the collapsed inner sleeve fits tightly over the colonoscope. A tight fit may be obtained, for example, by an inner sleeve having a collapsed diameter smaller than that of the colonoscope, for example 5%, 10%, 15%, 30% or intermediate, larger or smaller percentages smaller than a diameter of the colonoscope. In some embodiments, an expanded state of a sleeve lumen, suitable in diameter to receive a colonoscope insertion tube, comprises elastic stretching of at least 2 mm in lumenal diameter over an unstretched state. The elastic stretching is optionally of the inner sleeve, outer sleeve, or both.

In some embodiments, the colonoscope and attached add-on tubes which are held together by the sleeve assembly are inserted into the colon (208). Optionally, the colonoscope and tubes are steered together in the colon (210).

In some embodiments, if relative movement, to a certain extent, is allowed between one or more of the add-on tubes and the colonoscope, a user may adjust their relative positioning, for example by axially sliding an add-on tube, for example, an add-on tube configured for irrigation, to a distance beyond the colonoscope's distal head, such as to clear the colon area in front of the colonoscope's head. Optionally, the colonoscope's positioning in the sleeve can be adjusted in-vivo, for example by re-inflating the sleeve, advancing or pulling the colonoscope to a desired positioning in the sleeve, and collapsing the sleeve. Optionally, when performed in-vivo, a pressure level of inflation of the sleeve is set to a level lower than a pressure level of ex-vivo inflation.

In some embodiments, for example after the colonoscope and add-on tubes are withdrawn from the colon, the colonoscope is removed from the sleeve. Optionally, the add-on tubes are removed from the sleeve. Optionally, the sleeve comprising the add-on tubes is disposed. Alternatively, the add-on tubes are removed, and the sleeve is disposed. Optionally, the add-on tubes are sterilized for additional use.

Figures 3A, 3B:
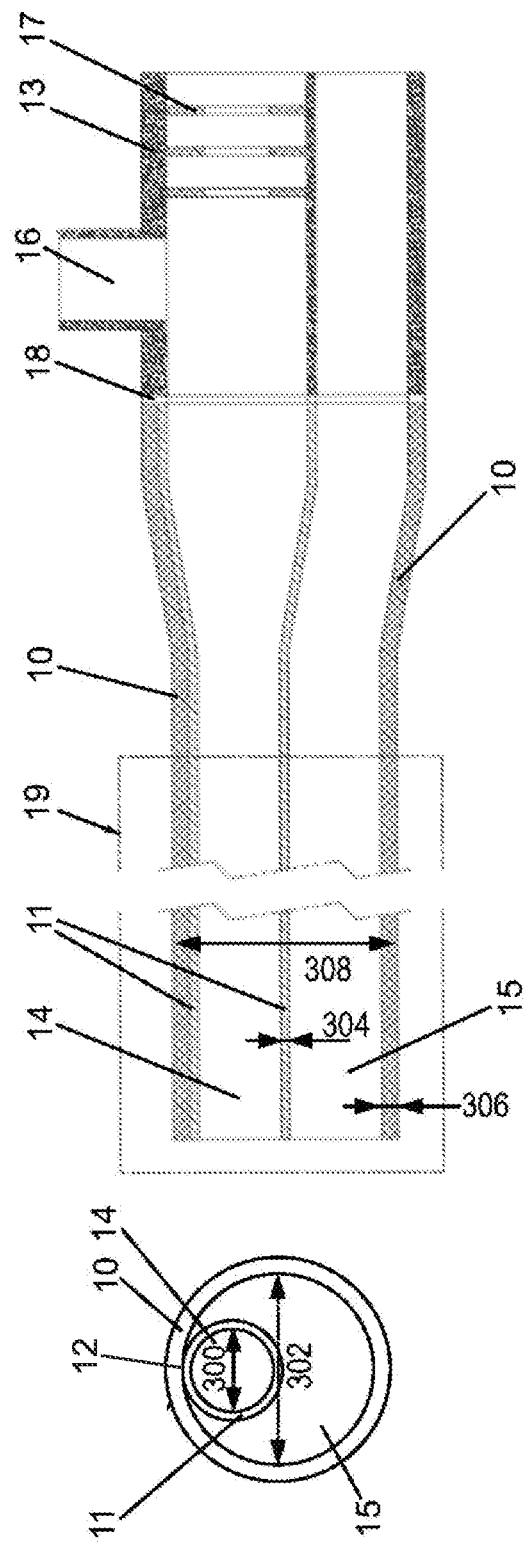
FIGS. 3A-3B show longitudinal (FIG. 3A) and transverse (FIG. 3B) cross sections of an exemplary sleeve assembly, according to some embodiments of the invention.

FIGS. 3A-3B show longitudinal (FIG. 3A) and transverse (FIG. 3B) cross sections of an exemplary sleeve assembly, according to some embodiments of the invention.

In some embodiments, the sleeve assembly comprises an inner sleeve 11, adapted for receiving a colonoscope. Inner sleeve 11 is circumferentially surrounded by an outer sleeve 10, including one or more add-on tubes. The exemplary configuration shown herein does not show add-on tubes, and those may be inserted into the sleeve, for example inserted into lumen 15 of outer sleeve 10, such as between the walls of inner sleeve 11 and outer sleeve 10. Alternatively, the add-on tubes are an integrated portion of the sleeve, for example, the tubes are formed during manufacturing of the sleeve.

Segment 19 of the sleeve assembly, for example as shown in FIG. 3A, is intended for insertion into the colon. Optionally, the length of segment 19 is in a range between, for example, 20 cm-200 cm, 50-165 cm, and/or 80-165 cm; for example, having a length of 50 cm, 150 cm, 165 cm, 180 cm or an intermediate, longer or shorter length.

In some embodiments, the inner sleeve and outer sleeve are attached to each other. For example, one or more circumferential segments of the wall of inner sleeve 11 are attached to the wall of outer sleeve 10. Optionally, a coupling 12 between the sleeves (for example as shown in FIG. 3B) extends along 5%, 10%, 15%, 25%, 45% or intermediate, larger or smaller portions of the circumference of inner sleeve 11. Optionally, the sleeves are attached to each other at more than one circumferential location, for example, 2, 3, 4, 5 or larger number of locations.

Additionally or alternatively, in some embodiments, coupling 12 comprises attachment along a line which is up to a few millimeters in width in the circumferential direction (for example, about 1 mm, 2 mm, 3 mm, 4 mm, 5 mm, or another greater, smaller, or intermediate width).

Optionally, coupling 12 extends continuously along a longitudinal axis of inner sleeve 11 and outer sleeve 10 for about 50%, 60%, 70%, 80%, 90%, or another greater, larger, or intermediate fraction of the overall length of segment 19 of the sleeve assembly, and/or of the sleeve assembly overall. Optionally, the extent of coupling 12 along the longitudinal axis is broken into a plurality of sub-segments.

In some embodiments, the longitudinal extent of the coupling excludes a section of the sleeve designated for covering a steering section of a colonoscope. This is a potential advantage to reduce interference with steering due, for example to asymmetric elastic properties induced by attachment between the sleeves.

In some embodiments, the coupling attachment 12 between the sleeves comprises, for example, welded attachment. Optionally, the sleeves are glued to each other. Additionally or alternatively, the sleeves are coupled to each other by other fastening means, such as flexible rings or wires. In some embodiments, coupling 12 includes a ratchet, which provides for, for example, relative movement of inner sleeve 11 within outer sleeve 10, and/or, for example, for restricting an expansion of inner sleeve 11.

In some embodiments, a diameter 300 of a lumen 14 of inner sleeve 11, for example as shown in FIG. 3B, in a non-expanded state, ranges between, for example, 8-12 mm, 3-10 mm, 5-18 mm, or intermediate, larger or smaller ranges. Optionally, diameter 300 is selected according to a diameter of a colonoscope, for example, diameter 300 can be 5%, 10%, 20% or intermediate, larger or smaller percentages smaller than a diameter of a colonoscope. In one example, for a colonoscope having a diameter of 12 mm, diameter 300 is 0.1-5 mm, 1-3 mm, 0.1-0.9 mm or intermediate, larger or smaller ranges smaller than the colonoscope's diameter in a non-expanded state.

In some embodiments, diameter 302 of lumen 15 of outer sleeve 10, for example as shown in FIG. 3B, ranges between, for example, 10-20 mm, such as 12 mm, 15 mm, 18 mm, or intermediate, larger or smaller diameters. Optionally, diameter 302 is selected according to a size and/or number of add-on tubes which lumen 15 accommodates.

In some embodiments, a thickness 304 of the wall of inner sleeve 11, for example as shown in FIG. 3A, is selected to be thick enough so as to reduce tearing by the colonoscope, for example during insertion of the colonoscope through, yet thin enough to reduce rigidity of the colonoscope. Optionally, thickness 304 ranges between 0.2-2 mm, such as 0.5 mm, 1 mm, 1.5 mm or intermediate, larger or smaller thicknesses.

In some embodiments, a thickness 306 of the wall of outer sleeve 10, for example as shown in FIG. 3A, is selected to be thin enough so as to reduce rigidity and/or to reduce a total diameter 308 of the sleeve assembly, for example as shown in FIG. 3A. Optionally, a total diameter 308 of the sleeve assembly ranges between, for example, 13-25 mm, such as 15 mm, 20 mm, 24 mm or intermediate, larger or smaller diameters. Optionally, a thickness 306 of the wall of outer sleeve 10 ranges between 0.2-2 mm.

In some embodiments, the proximal ends of inner sleeve 11 and outer sleeve 10 are enclosed within a proximal housing 13, for example as shown in FIG. 3A.

Optionally, housing 13 is rigid. Optionally, housing 13 is made of, for example, polyurethane. Optionally, housing 13 connects between the sleeve assembly and the colonoscope's handle. Optionally, housing 13 connects between one or more components of the sleeve assembly, such as add-on tubes, and a workstation.

Optionally, housing 13 is rigid enough to transfer torsion towards a distal end of the sleeve assembly, for example during steering in the colon.

In some embodiments, housing 13 comprises one or more openings, such as opening 16. Optionally, air and/or liquid used for inflating inner sleeve 11 are delivered through opening 16, for example by connecting opening 16 to a pump.

Optionally, a valve is positioned at opening 16, for controlling the flow in and/or out of the sleeve.

In some embodiments, one or more sealing rings 17, for example as shown in FIG. 3A, are positioned in the sleeve assembly, for example, positioned within inner sleeve 11. Optionally, sealing rings 17 reduce or prevent leakage of air and/or liquid from the inflated sleeve, for example during insertion of the colonoscope through.

In some embodiments, the sleeve assembly is made of a flexible material, such as polyurethane (PU), Silicon. Optionally, the material is selected to be elastic enough to reduce rigidity of the complete colonoscope-add-on tubes assembly, enabling steering in the colon, and, on the other hand, the material is selected to be rigid enough to maintain the add-on tubes coupled to the colonoscope, and restrict movement of the tubes with respect to the colonoscope.

In some embodiments, at least a portion of the sleeve assembly, for example at least 40%, 60%, 80% or intermediate, larger or smaller percentages of the length of the sleeve, for example segment 19, is made of a transparent material. Optionally, scale marks on a colonoscope are visible through the transparent sleeve. Optionally, a portion of the sleeve defines a viewing window through which the scale marks are visible.

In some embodiments, the sleeve assembly is manufactured using laser welding and/or extrusion techniques.

In some embodiments, outer sleeve 10 is coated by friction-reducing material such as Parylene C, which may facilitate insertion into the colon.

In some embodiments, outer sleeve 10 is formed of multiple layers of materials having different friction coefficients. In an example, an outer layer of sleeve 10 which may come in contact with the walls of the colon comprises a material having a smaller friction coefficient than the friction coefficient of a material forming an inner layer of sleeve 10. Optionally, a multi layered sleeve such as double layered sleeve is manufactured using co-extrusion technology. A sleeve comprising two or more materials having different friction properties may be effective to reduce friction between the sleeve and the walls of the colon by an outer layer comprising a first friction coefficient which is smaller than a friction coefficient of an inner layer of the sleeve, which in turn may be effective to increase the contact strength when holding the add-on tubes to the colonoscope and/or to contribute to unified movement of the sleeve and the colonoscope positioned within it.

A sleeve, for example as described herein, is one example of an apparatus for coupling a colonoscope to one or more add-on tubes. It is noted that in some embodiments, an element having a general tubular geometry which is suitable for receiving a colonoscope, for example a spring element, may be used for coupling between the colonoscope and add-on tubes.

It is further noted that in some embodiments, a tubular element may comprise shape memory materials, for example nitinol. Optionally, collapsing and/or expanding of a tubular element may include applying stress, a change in temperature, an electric or magnetic field to induce changes in the shapeable material, causing the material to expand and/or collapse.

Figure 4:
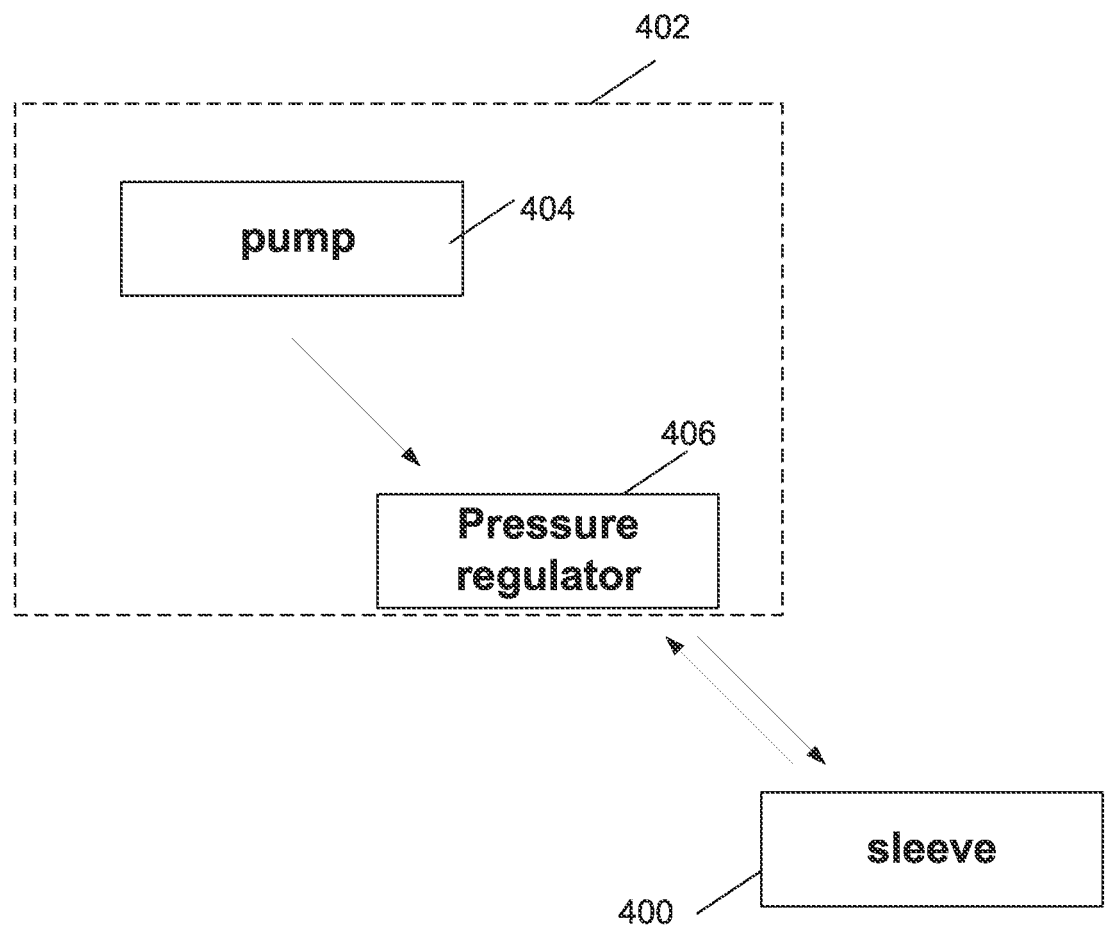
FIG. 4 is a schematic diagram of a system comprising an inflation module for coupling between a colonoscope and one or more add-on tubes, according to some embodiments of the invention.

FIG. 4 is a schematic diagram of a system comprising an inflation module for coupling between a colonoscope and one or more add-on tubes, according to some embodiments of the invention.

In some embodiments, a sleeve 400 for example as described herein is connected to an inflation module 402. Optionally, inflation module 402 comprises a pump 404, such as an air pump. Optionally, inflation module 402 comprises a pressure regulator 406.

In some embodiments, pump 404 is configured for supplying an air pressure of, for example 300-600 mbar, for example 300 mbar, 350 mbar, 450 mbar, 550 mbar or intermediate, higher or lower pressure levels. Optionally, pressure regulator 406 modifies the flow of air or liquid from pump 404. Optionally, the pressure in the sleeve is dynamically adjusted by pressure regulator 406.

In some embodiments, sleeve 400 (or a portion of it, such as an inner sleeve) is inflated to a maximal pressure of, for example, 300 mbar, 400 mbar, 350 mbar, or intermediate, higher or lower pressure levels. Optionally, different portions of the sleeve are inflated to different pressure levels. In some embodiments, selective inflation is performed. For example, gradual inflation of the sleeve (e.g. step wise inflation of the sleeve, one segment after another) is performed during insertion of the colonoscope through the sleeve. A potential advantage of selectively inflating portions may include reducing perforation of the sleeve, for example by the colonoscope. Another potential advantage may include obtaining a better fit of the sleeve to the colonoscope, after collapsing.

Optionally, sleeve 400 is inflated until reaching a diameter suitable for facilitating insertion of the colonoscope through.

In some embodiments, inflation module 402 is configured for applying vacuum to the sleeve, for example to remove air after positioning of the colonoscope in the sleeve to collapse the sleeve.

Figure 5:
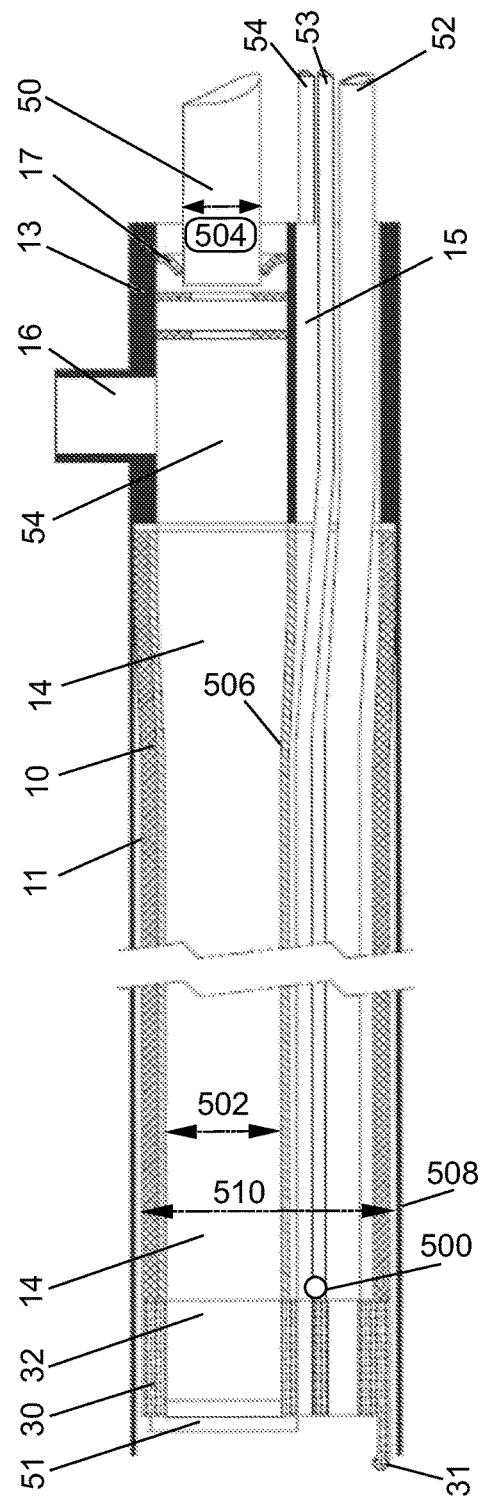
FIG. 5 is an exemplary configuration of a sleeve assembly comprising one or more add-on tubes and configured for receiving a colonoscope, according to some embodiments of the invention.

FIG. 5 shows an exemplary configuration of a sleeve assembly comprising one or more add-on tubes and configured for receiving a colonoscope to couple between the tubes and the colonoscope, according to some embodiments of the invention.

In some embodiments, a plurality of add-on tubes such as 2, 3, 4, 6, 9, or intermediate, larger or smaller number are comprised within the sleeve assembly. For example, as shown in this figure, 3 add-on tubes 52, 53 and 54 are positioned within lumen 15 of outer sleeve 10. Optionally, tubes 52, 53 and 54 vary in diameter and/or length, for example according to their function. In an example, tube 52 is configured for evacuation of fecal matter from the colon; tube 53 is configured for sensing, such as sensing of pressure in the colon, for example by having one or more pressure sensors 500 configured at a distal portion of the tube; and tube 54 is configured for irrigation of the colon, and may comprise jet-forming distal head (not shown in this figure). Optionally, the proximal ends of tubes 52, 53 and 54 are connected to a work station (not shown in this figure).

In some embodiments, colonoscope 50 is received within lumen 14 of inflated inner sleeve 11. Optionally, in an inflated state, a diameter 502 of lumen 14 along at least some segments of inner sleeve 11 is at least 5%, 10%, 20%, 40% or intermediate, larger or smaller percentages larger than a diameter 504 of colonoscope 50. For example, in the inflated state, diameter 502 ranges between 13-25 mm, such as 14 mm, 22 mm, 24 mm or intermediate, larger or smaller diameters.

In some embodiments, for example prior to inflation, a cap 51 is placed over a distal opening of inner sleeve 11. Optionally, cap 51 seals lumen 14 during inflation, so that the inserted air causes a radially outward expansion of the walls 506 of sleeve 11. In some embodiments, once colonoscope 50 is positioned within inner sleeve 11, cap 51 is removed, allowing air to exit the sleeve and/or enabling the advancement of a distal head of colonoscope 50 until it is aligned with the distal opening of the sleeve or protrudes externally from the distal opening.

In some embodiments, cap 51 is coupled to the sleeve by a threaded connection, and is unscrewed from the sleeve. Additionally or alternatively, cap 51 is attached by a breakable connection, and is broken off to allow air to exit the sleeve.

In some embodiments, the radial expansion, for example obtained by inflation, is non symmetrical. For example, a circumferential portion of the inner sleeve 11 that is not attached to outer sleeve 10 may expand more than the attached portion.

In some embodiments, a housing 30 is configured at a distal end of the sleeve assembly. Optionally, housing 30 encases the distal ends of tubes 52, 53 and 54, and/or the distal end of colonoscope 50. Optionally, housing 30 encases the distal openings of inner sleeve 11 and outer sleeve 10. In some embodiments, housing 30 aligns the distal ends of tubes 52, 53 and 54 with respect to the distal head of colonoscope 50. Optionally, housing 30 comprises one or more extensions 31, for example extending beyond a distal opening of lumen 14 of the sleeve, for example to a distance ranging between 0.1 mm-10 cm beyond a distal opening of lumen 14.

Optionally, extension 31 reduces or prevents damage to tissue such as colon wall tissue when the colonoscope is in the colon.

In some embodiments, housing 30 is made of a flexible material, for example polyurethane. In some embodiments, housing is formed of a material having shore hardness value ranging between 40-90, such as 50, 70, 85 or intermediate, larger or smaller values. A potential advantage of a flexible housing 30 may include reducing damage to tissue such as the walls of the colon during insertion of the colonoscope and attached add-on tubes. Another potential advantage of a flexible housing may include inflating the inner sleeve without having to remove the housing, as the elasticity of housing 30 provides for expansion. Alternatively, in some embodiments, distal housing 30 is rigid.

In some embodiments, an external sleeve 508 is positioned over the sleeve assembly, for example during inflation. Optionally, external sleeve 508 is formed of a rigid material, such as hardened polyurethane. Potentially, this prevents over-expansion of the sleeve assembly. For example, external sleeve 508 may prevent over-expansion of outer sleeve 10 which is, in some embodiments, caused to expand as a result of inflation of inner sleeve 11. Optionally, external sleeve 508 maintains a total diameter 510 of the sleeve assembly under, for example, 25 mm, 20 mm, 30 mm, or intermediate, larger or smaller diameters. Optionally, external sleeve 508 is removed before insertion of the sleeve assembly to the colon, for example after collapsing.

In some embodiments, one or more tubes 52, 53 and/or 54 are held to colonoscope 50, for example, at one or more longitudinal segments of the colonoscope, by an arrangement other than the sleeve. For example, the tubes are attached to the colonoscope using tape, for example tape wrapped around both the colonoscope and the tubes to hold them together. In some embodiments, the sleeve assembly holds the tubes to the colonoscope along a first longitudinal segment of the sleeve, and other fastening means such as tape couple between the colonoscope and the tubes along a second longitudinal segment. In an example, a distal portion of colonoscope 50 extending from a distal end in a proximal direction to, for example, 5%, 10%, 15% of the colonoscope's length is attached to the tubes using one or more tape wraps, and the rest of the colonoscope is coupled to the tubes by the sleeve assembly.

Figure 6C:
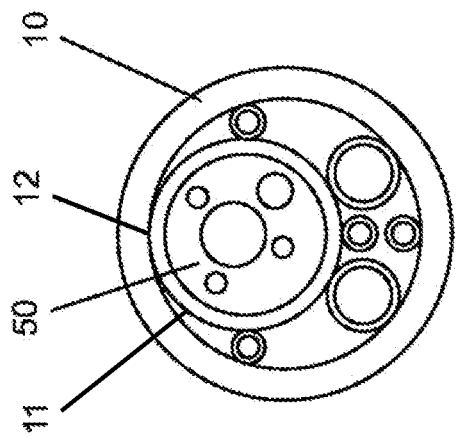
FIGS. 6A-C are drawings of a set up procedure for coupling between a colonoscope and one or more add-on tubes using a sleeve assembly, according to some embodiments of the invention.
Figure 6B:
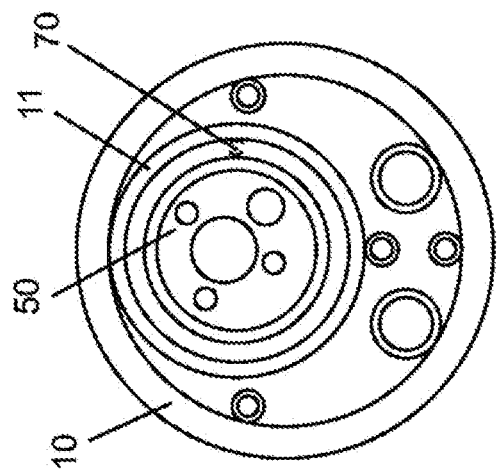
Figure 6A:
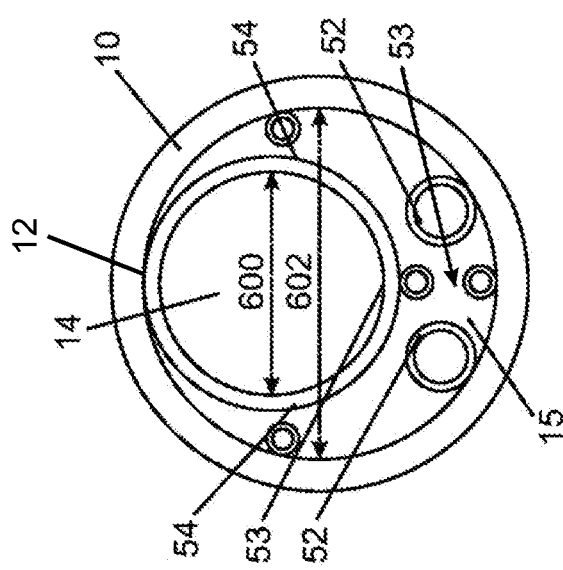

FIGS. 6A-6C are drawings of a set up procedure for coupling between a colonoscope and one or more add-on tubes using a sleeve assembly, according to some embodiments of the invention.

FIG. 6A shows a cross section of the sleeve assembly before insertion of colonoscope 50 through. Add-on tubes 52, 53 and 54 are configured within lumen 15, between inner sleeve 11 and outer sleeve 10. In this example, a set of each type of tube is shown (i.e. two evacuation tubes 52, two sensing tubes 53, and two irrigation tubes 54). Alternatively, different amounts and/or different types of tubes may be used. The configuration for example as shown in FIG. 6A shows lumen 14 of inner sleeve 11 before inflation.

FIG. 6B shows an inflated lumen 14 of inner sleeve 11. A radial gap 70 is formed between an original location of the wall of inner sleeve 11, for example with respect to a wall of outer sleeve 10, as shown for example in FIG. 6A and indicated by the dashed circle in FIG. 6B, and a location of the wall of inner sleeve 11 after inflation. Optionally, radial gap 70 ranges between, for example, 0.2-8 mm. In some embodiments, colonoscope 50 is advanced through lumen 14 of inflated inner sleeve 11. Optionally, the distanced walls of inflated inner sleeve 11 provide for smooth delivery of the colonoscope through the lumen.

In some cases, radially outward force is exerted on the add-on tubes and/or on the wall of outer sleeve 10 by the walls of inflated inner sleeve 11. Optionally, outer sleeve 10 is caused to expand radially as a result of the applied force.

FIG. 6C is a cross section of the sleeve assembly following collapsing. The wall of inner sleeve 11 is closely fitted on colonoscope 50. Gap 70 is reduced, for example reduced to fit a diameter of colonoscope 50, such as a 12 mm diameter, 9 mm diameter, 15 mm diameter, or intermediate, larger or smaller diameters. Optionally, gap 70 is fully reduced, and a diameter 600 of lumen 14 of inner sleeve 11 returns to its initial size, for example as shown in FIG. 6A. Optionally, gap 70 is fully reduced, and a diameter 600 of lumen 14 of collapsed inner sleeve 11 is further reduced to a size smaller than its initial size, for example 2-5 mm smaller than its initial size.

In some embodiments, add-on tubes 52, 53 and 54 are held by outer sleeve 10 radially closer to colonoscope 50. Optionally, collapsing increases a contact area between the wall of inner sleeve 11 and the wall of outer sleeve 10, for example a circumferential segment of coupling 12 is effectively lengthened.

Optionally, for example due to the elasticity of outer sleeve 10, collapsing of inner sleeve 11 causes the wall of outer sleeve 10 to contract. Optionally, a diameter 602 of lumen 15 of outer sleeve 10 is reduced with respect to its initial position, for example as shown in FIG. 6A, for example reduced by 2-5 mm, 0.2-4 mm, 2-5 mm, or intermediate, larger or smaller ranges.

Figure 7:
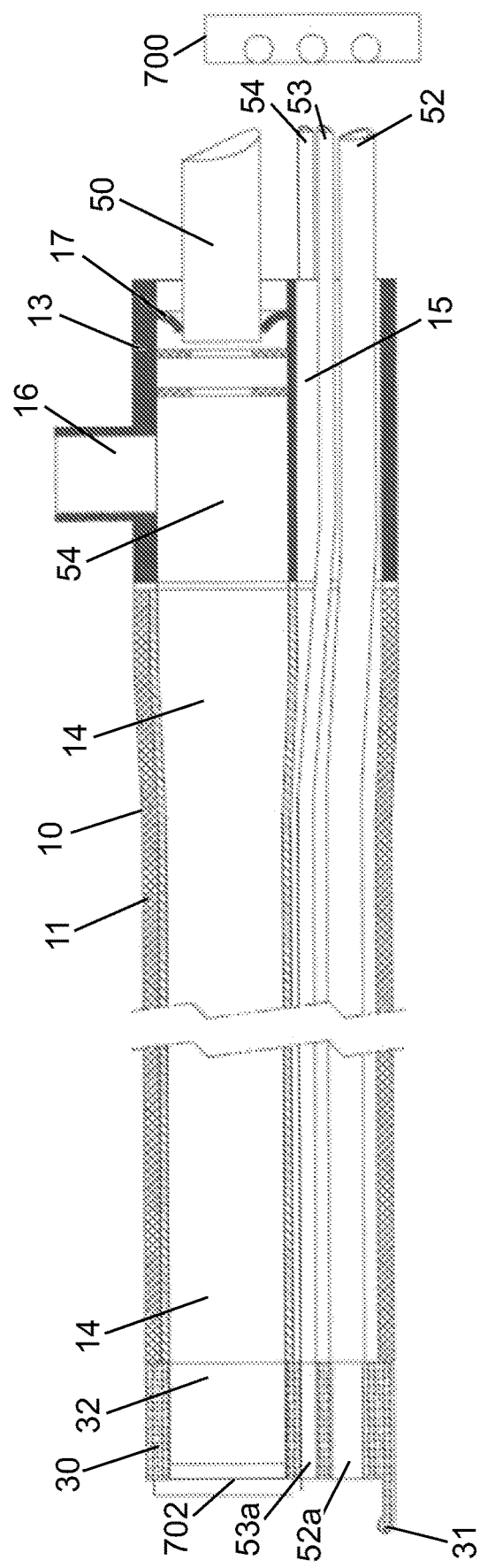
FIG. 7 is a drawing of a colonoscope coupled to one or more add-on tubes by a sleeve, according to some embodiments of the invention.

FIG. 7 shows a colonoscope coupled to one or more add-on tubes by a sleeve, according to some embodiments of the invention.

In some embodiments, a proximal end of tubes 52, 53 and 54 is connected to a workstation 700. Optionally, workstation 700 comprises, for example, one or more of a liquid tank for supplying liquid such as water to irrigation tube 54, a vacuum source (or a connection to an external vacuum source) for supplying vacuum to evacuation tube 52, circuitry for example for acquiring data from one or more sensors of sensing tube 53. Optionally, the add-on tubes extend in the proximal direction along the colonoscope's umbilical cord (not shown in this figure), until reaching workstation 700. In some embodiments, the add-on tubes attached at one or more longitudinally distributed locations to the umbilical cord, for example by a tape wrap, a clasp, or other attachment means, to prevent them from interfering with handle movement or the like.

In some embodiments, the distal ends 52a, 53a of the add-on tubes are aligned with a plurality of distal openings in distal housing 30. Optionally, distal ends 52a, 53a are aligned with a distal head 702 of the colonoscope. Additionally or alternatively, housing 30 is constructed to hold one or more add-on tubes beyond head 702 of the colonoscope in a distal direction, and/or to hold one or more add-on tubes short of head 702 in a proximal direction.

Optionally, distal extension 31 protrudes to a distance beyond the distal openings of housing 30.

In some embodiments, colonoscope 50 is advanced towards a distal end of sleeve 11. Optionally, the colonoscope is advanced until a head 702 configured at a distal end of the colonoscope is aligned with a distal opening of distal housing 30, for example as shown herein. Additionally or alternatively, the colonoscope is advanced until reaching a cap positioned at a distal end of the sleeve. Additionally or alternatively, the colonoscope is advanced until colonoscope head 702 protrudes externally from a distal opening of the sleeve.

Figure 8A:
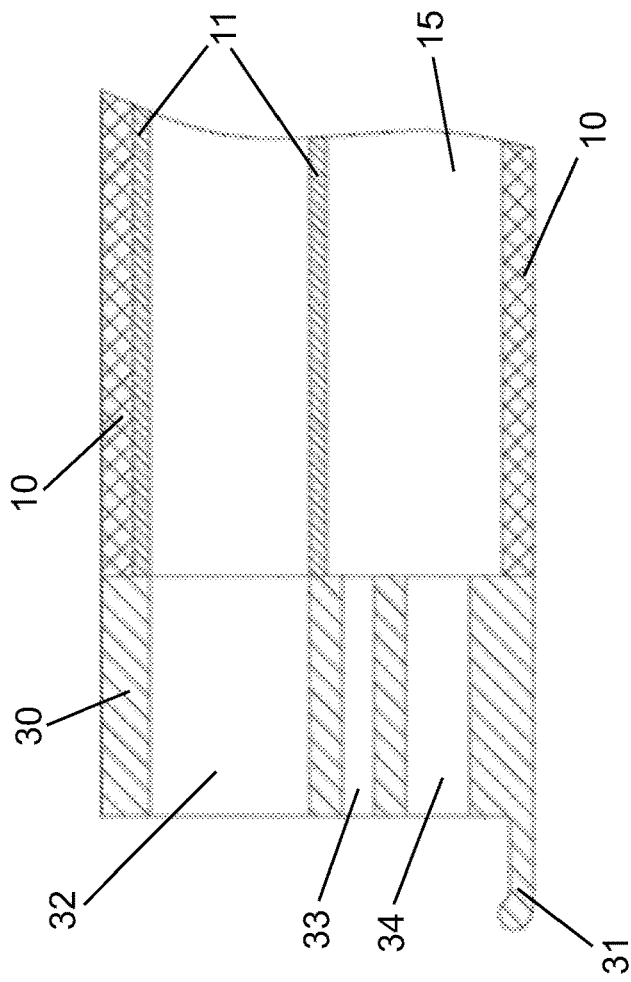
FIGS. 8A-8B show a side view (FIG. 8A) and a front view (FIG. 8B) of a distal housing of a sleeve assembly, according to some embodiments of the invention.
Figure 8B:
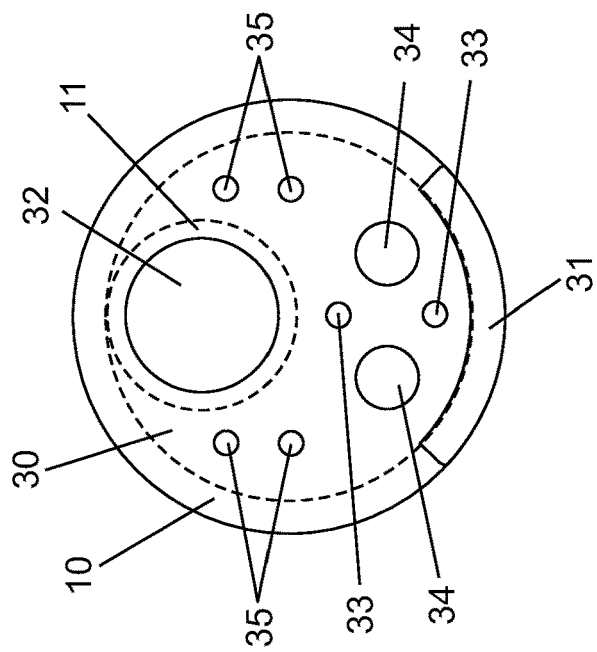

FIGS. 8A-8B show a side view (FIG. 8A) and front view (FIG. 8B) of a distal housing of a sleeve assembly, according to some embodiments of the invention. In some embodiments, housing 30 is formed with a plurality of distal openings, for example opening 32 for delivering a colonoscope, and/or openings 33, 34 and/or 35 (shown for example in FIG. 8B) for delivering add-on tubes. Optionally, a distal opening is formed with a circular profile, an elliptic profile, a square profile, a rectangular profile, a triangular profile or any other shape suitable compatible with a distal end of an add-on tube or a distal end of the colonoscope.

FIGS. 9A-9F show various schematic configurations for positioning one or more add-on tubes with respect to a colonoscope, according to some embodiments of the invention.

In some embodiments, one or more add tubes 900, 902 are oriented with respect to a colonoscope 904. Optionally, the tubes are positioned with respect to a longitudinal axis 906 of the colonoscope. Additionally or alternatively, the tubes are oriented with respect to a handle of the colonoscope.

The exemplary schematic configurations shown herein may correspond with a collapsed configuration of the sleeve, in which the tubes are held in proximity the colonoscope. Various embodiments may include a different number of add-on tubes, and/or different orientation configurations with respect to the colonoscope.

Figure 9F:
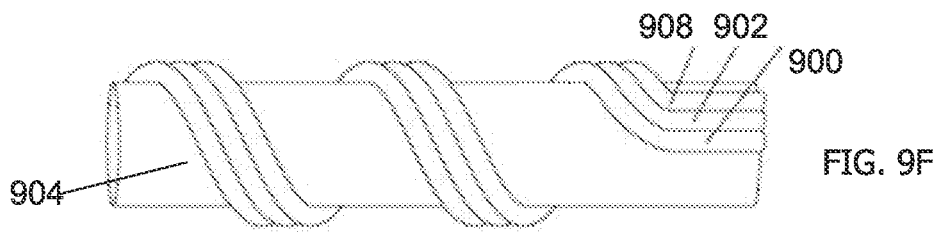
FIGS. 9A-9F show various schematic configurations for positioning one or more add-on tubes with respect to a colonoscope, according to some embodiments of the invention.
Figure 9E:
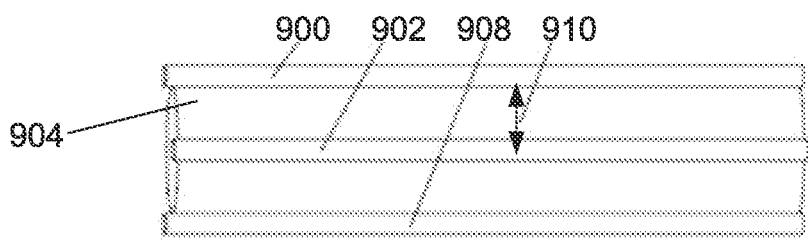
Figure 9D:
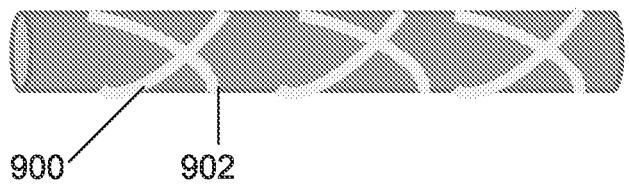
Figure 9C:
Figure 9B:
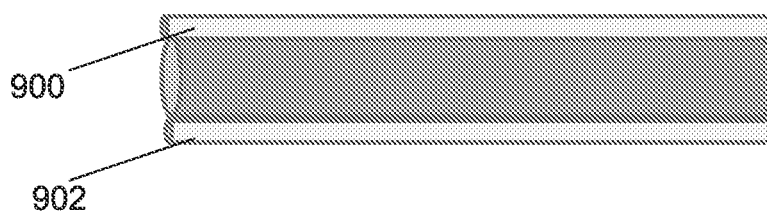
Figure 9A:
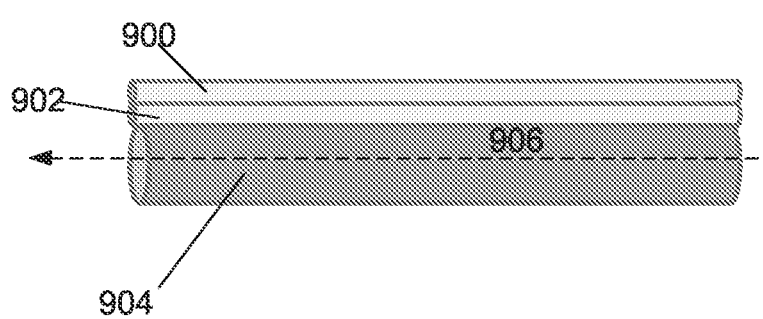

FIG. 9A shows tubes 900, 902 aligned in parallel to longitudinal axis 906 of the colonoscope, the tubes being positioned on a first side of axis 906, according to some embodiments.

FIG. 9B shows tubes 900, 902 aligned in parallel to longitudinal axis 906 of the colonoscope, the tubes positioned on opposite sides of axis 906, according to some embodiments.

FIG. 9C shows tube 900 helically wound around colonoscope 904, according to some embodiments.

FIG. 9D shows tubes 900 and 902 interlaced with each other and wrapped around the colonoscope, according to some embodiments.

FIG. 9E shows a plurality of tubes such as tubes 900, 902, 908 arranged circumferentially around colonoscope 904. Optionally, the tubes are equally spaced from each other, with a distance 910 between them. Alternatively, the tubes are arranged with varying distances between them.

FIG. 9F shows a plurality of tubes such as 900, 902 and 908 spirally wounded around colonoscope 904. A potential advantage of spirally winded tubes may include facilitating insertion into the colon, as often the physician rotates the colonoscope around its axis, and spirally winded tubes would reduce the resistance to rotation, for example as compared to parallel extending tubes.

In some embodiments, the one or more tubes are arranged to least affect the steering of the colonoscope. Optionally, there is a pre-defined orientation of the handle with respect to the insertion tube of the colonoscope, and the tubes are positioned to minimize their effect on, for example, steering of the colonoscope, for example by being wound around the colonoscope.

In some embodiments, for example when a sleeve assembly comprising an inner sleeve and an outer sleeve is used, an inner surface of the outer sleeve defines one or more elongated grooves or paths in which the add-on tubes are received. Optionally, the grooves are parallel to the longitudinal axis of the inner sleeve, so that the add-on tubes are aligned in parallel to the colonoscope that is received within the inner sleeve. Additionally or alternatively, the grooves extend at an angle (e.g. twisted around) and/or are otherwise arranged with respect to the inner sleeve.

Figure 10A:
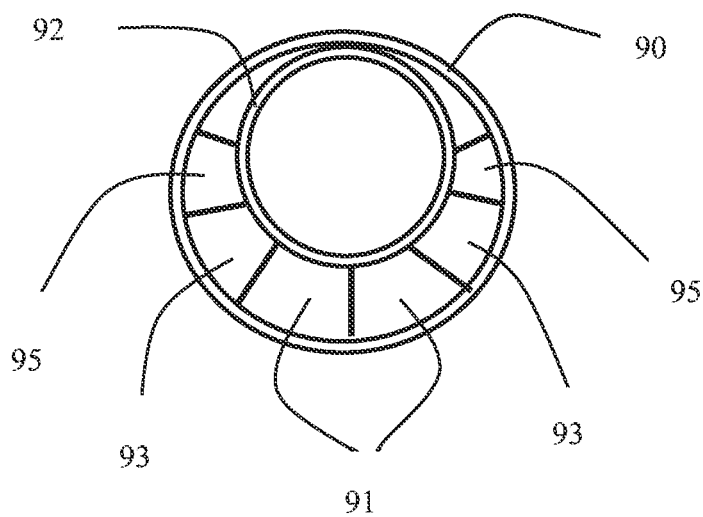
FIGS. 10A-10B are various alternative configurations of a sleeve, according to some embodiments of the invention.
Figure 10B:
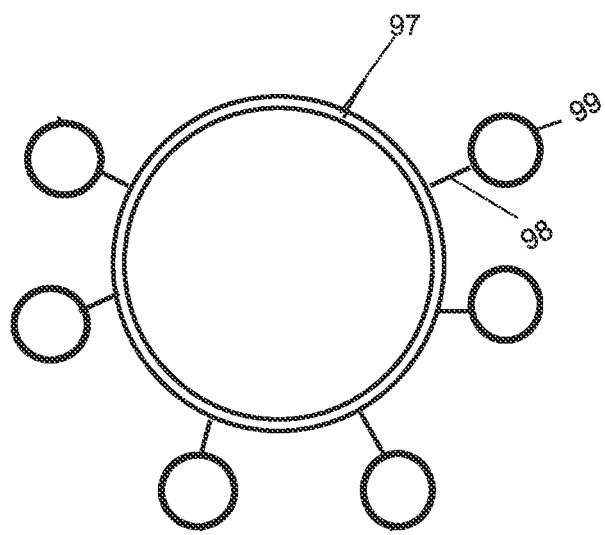

FIGS. 10A-10B are various alternative configurations of a sleeve, according to some embodiments of the invention.

FIG. 10A shows a cross section of an outer sleeve 90 encompassing an inner sleeve 92. In some embodiments, a lumen between outer sleeve 90 and inner sleeve 92 is divided into a plurality of compartments such as 93, 94, and 95. Optionally, one or more walls and/or other types of barriers are positioned between the inner and outer sleeves to divide the lumen into compartments. In some embodiments, compartments 93, 94 and/or 95 extend axially along the sleeve, thereby potentially being coaxial with a colonoscope positioned within inner sleeve 92.

In some embodiments, the compartments are functionally equivalent to a set of add-on tubes. In an example, compartment 91 is used for evacuation of matter from the colon; compartments 93 are used for sensing; compartments 95 are used for irrigation.

FIG. 10B shows a cross section of a sleeve 97 comprising a plurality of extensions 98, each extension leading to one or more lumens 99, for example configured as tubes. In some embodiments, extensions 98 are arranged circumferentially, extending from sleeve 97 in a radially outwards direction.

Optionally, a lumen 99 that is coupled to sleeve 97 by an extension 98 extends longitudinally along inner sleeve 97. In some embodiments, lumen 99 serves for one or more of, for example, irrigation, sensing, and/or evacuation from the colon, alongside a colonoscope that is positioned within sleeve 97.

Optionally, such as in the configuration described herein, a need for an outer sleeve is reduced, as the lumens 99 are held to inner sleeve 97 by extensions 98.

In some embodiments, an extension 98 is rigid. Alternatively, extension 98 is elastic. In some embodiments, extensions 98 can be folded towards the center of sleeve 97, for example to a position in which tubes 99 are moved to fit closely around the sleeve. Folding and/or twisting the extensions relative to the sleeve to bring the add-on tubes radially closer to the sleeve may be advantageous when inserting the sleeve assembly, comprising the colonoscope and add-on tubes, into the colon. In some embodiments, extensions 98 bounce back to an extended position when inside the colon.

In some embodiments, a length of an extension 98 is selectable and/or controllable. Optionally, extension 98 is structured as a telescopic pole, providing for distancing or approximating lumen 99 to or from sleeve 97. Optionally, a length of extension 98 ranges between, for example, 0.5 mm to 20 mm, such as 2 mm, 10 mm, 15 mm, or intermediate, longer or shorter lengths. In some embodiments, extensions 98 vary in length.

In some embodiments, for example if extension 98 is in the form of a cable, a diameter of the cable may range between, for example, 2-5 mm.

In some embodiments, configurations for example as described herein are manufactured using an extrusion technology.

In some embodiments, extension 98 is formed of a similar material as sleeve 97 is formed of, for example comprising polyurethane.

In some embodiments, a tube defining lumen 99 is formed of a soft material, to reduce damage to the walls of the colon. Optionally, the tubes are coated by a lubricating material, such as Vaseline, to smoothly glide into the colon.

Figure 11:
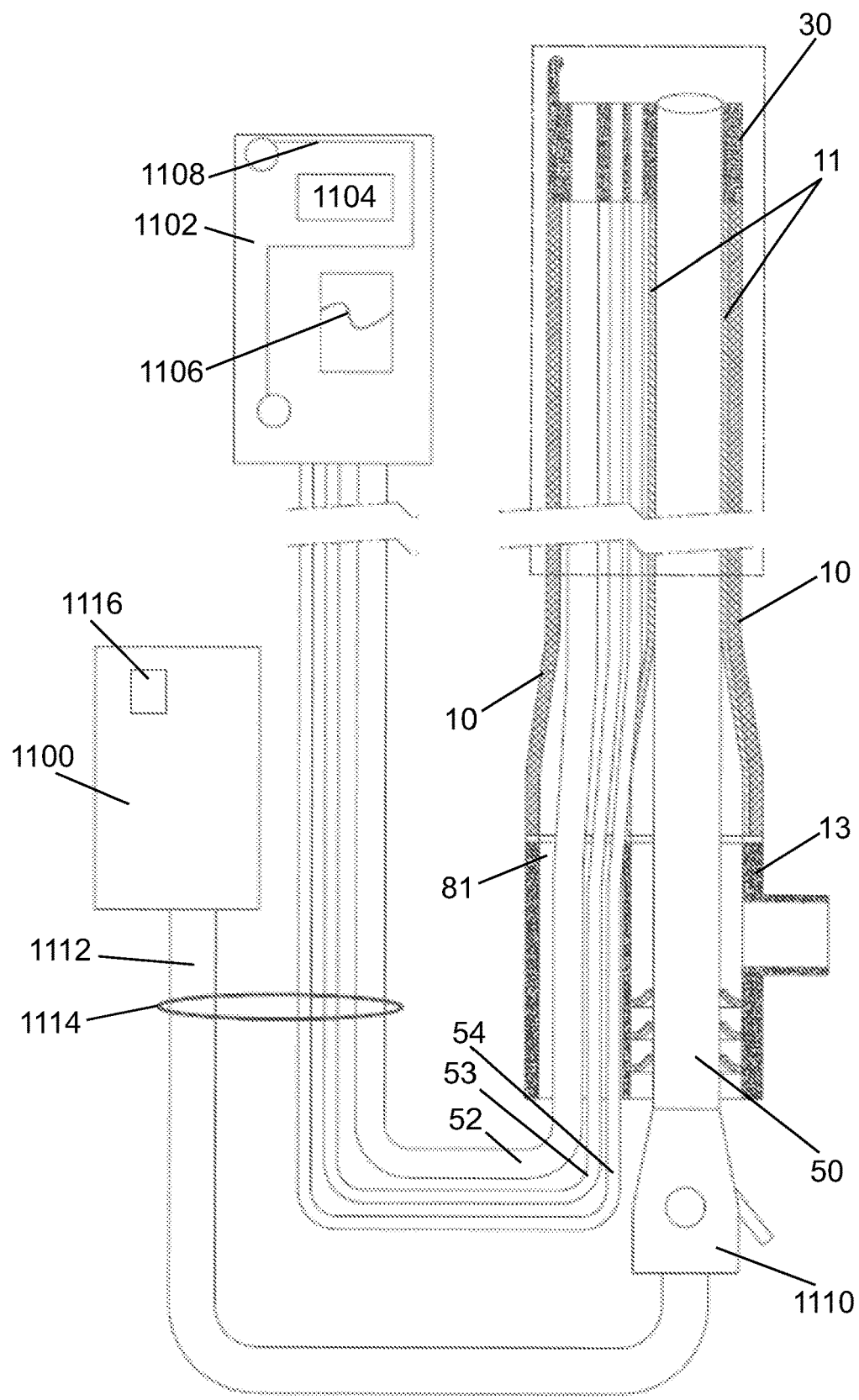
FIG. 11 shows a colonoscopy system in which the colonoscope's insertion tube is coupled to a plurality of add-on tubes by a sleeve, according to some embodiments of the invention.

FIG. 11 shows a colonoscopy system in which the colonoscope's insertion tube is coupled to a plurality of add-on tubes by a sleeve, according to some embodiments of the invention.

In some embodiments, a colonoscopy system comprises a colonoscope 50 coupled, on a proximal end, to a colonoscope workstation 1100. In some embodiments, workstation 1100 comprises a controller 1116, adapted for performing one or more function associated with operation of colonoscope 50. In some embodiments, controller 1116 is configured to activate and/or perform functions such as one or more of detecting pressure changes, detecting a clog in a colonoscope, assessing changes in flow in the colonoscope, activating evacuation of fecal matter, activating irrigation of the colon with fluids and/or gas, and/or other functions involved with operation of the colonoscope.

As further shown in this figure, a set of add-on tubes such as tubes 52, 53 and/or 54 are coupled to colonoscope 50 by a sleeve, including, for example, an inner sleeve 11 in which the colonoscope is received, and an outer sleeve 10 holding the add-on tubes to the colonoscope. In some embodiments, the add-on tubes are attached, on their proximal ends, to a workstation 1102. Optionally, the add-on tubes are operated through workstation 1102.

In some embodiments, workstation 1102 comprises a vacuum source 1104 and/or one or more liquid tanks 1106, which are connectable to the add-on tubes. In some embodiments, workstation 1102 comprises circuitry 1108, such as circuitry configured for operating the add-on tubes, for example configured for activating and/or ceasing vacuum through the one or more tubes. In some embodiments, the circuitry is configured for acquiring data from one or more sensors, such as sensors configured within and/or mounted externally to the add-on tubes and/or the colonoscope.

In some embodiments, colonoscope workstation 1100 and add-on tube workstation 1102 are physically and/or operatively combined together to a single workstation.

In some embodiments, a handle 1110, adapted for operation by a user such as a physician, is configured between the insertion tube of colonoscope 50 and the umbilical cord 1112. Alternatively, the handle is configured along the length of colonoscope 50 at a different location.

In some embodiments, the add-on tubes are connected, for example in proximity to their proximal ends, to the colonoscope's umbilical cord 1112.

Optionally, the add-on tubes are tied to the umbilical cord by a connecting structure such as a cable 1114. In some embodiments, a clasp, tape, or any other element suitable for attaching the add-on tubes to the colonoscopy is used. A potential advantage of coupling between the add-on tubes and the umbilical cord of the colonoscope may include reducing interfering of the add-on tubes during operation, facilitating maneuvering of the colonoscope by a physician.

In some embodiments, one or more additional coupling structures such as proximal housing 13 and/or distal housing 30 provide a connection between the add-on tubes and the colonoscope at various locations along the length of the add-on tubes and/or colonoscope, optionally in addition to the coupling provided by the sleeve.

Figure 12A:
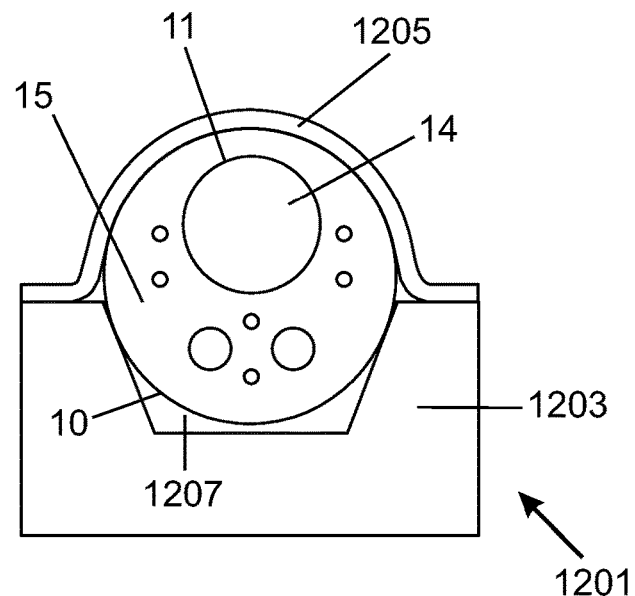
FIGS. 12A-12B illustrate an exemplary jig for setting up the colonoscope and add-on tubes assembly, according to some embodiments of the invention.
Figure 12B:
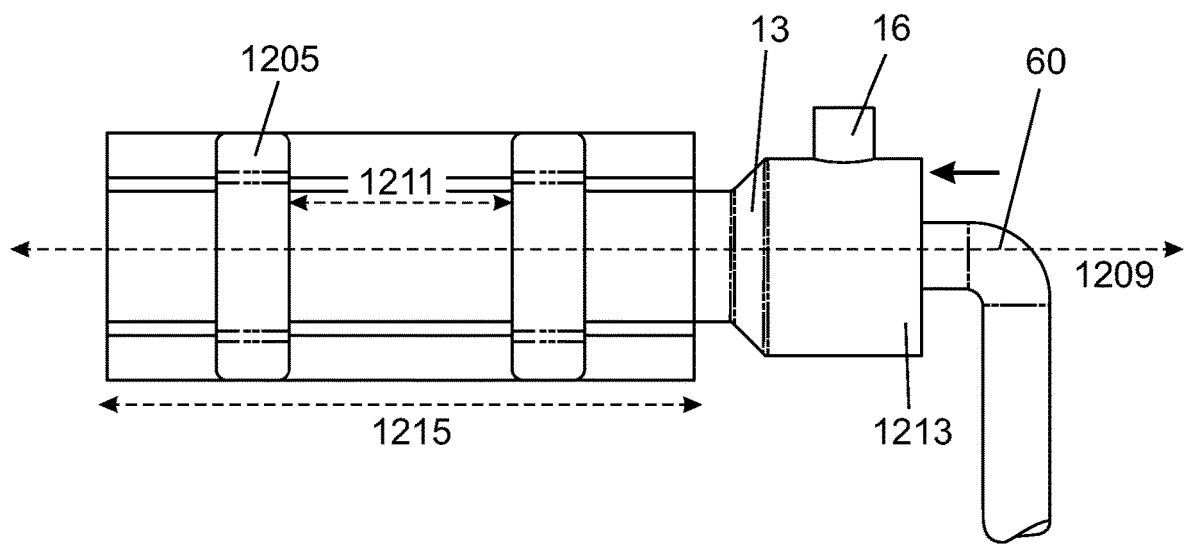

FIGS. 12A-B illustrate an exemplary track jig 1201 for setting up the colonoscope and add-on tubes assembly, according to some embodiments of the invention. In some embodiments, a jig 1201 comprises a base portion 1203, and one or more fasteners 1205 for holding the sleeve assembly to the base portion during set up.

In some embodiments, base portion 1203 is formed as an elongated, linear track, defining a recess 1207 in which the sleeve is received. Optionally, for example as shown in the transverse cross section of the jig in FIG. 12A, recess 1207 comprises a substantially trapezoidal cross section profile, but may be otherwise shaped, for example having a semi-circle cross section profile, a rectangular cross section profile, or other profile suitable for receiving the sleeve assembly.

In some embodiments, the sleeve assembly, for example comprising an inner sleeve 11, in which a colonoscope is received, and an outer sleeve 10 which encompasses the one or more add-on tubes, is introduced into recess 1207 of the jig, and is positioned to extend lengthwise within recess 1207.

In some embodiments, outer sleeve 10 and/or inner sleeve 11 are inflated, for example by connecting an air pump to deliver air through opening 16, configured, for example, at a proximal housing 13 of the sleeve assembly. In some embodiments, outer sleeve 10 is inflated until its radial and/or axial expansion is restricted by the one or more fasteners 1205.

In some embodiments, a colonoscope 50 is introduced into the sleeve assembly, for example through a proximal opening 1213 of housing 13. In some embodiments, colonoscope 50 is advanced within lumen 14 of inner sleeve 11, in a way that it lays coaxially to jig 1201. A potential advantage of threading the colonoscope through a sleeve assembly which is held firmly by the jig may include facilitating advancing the colonoscope through, as the sleeve is restrained from moving during insertion.

Providing a temporary fixation of the sleeve combined with inflating the sleeve to reduce friction during insertion may accelerate threading of the colonoscope into the sleeve, potentially reducing preparation time before the colonoscopy procedure.

In some embodiments, fasteners 1205 extend transversely over recess 1207. In some embodiments, fasteners 1205 are suitable to keep the sleeve assembly from moving out of recess 1207. Additionally or alternatively, fasteners 1205 restrict an extent of inflation of the sleeve assembly. Additionally or alternatively, fasteners 1207 limit axial movement of the sleeve assembly within recess 1207, for example by a textured inner surface of a fastener 1207, facing the colonoscope, which is effective to increase friction between the sleeve and the fastener. Optionally, the textured inner surface of fastener 1207 comprises, for example, bumps, protrusions, and/or other roughening texture. Alternatively, some movement of the sleeve assembly, such as axial back and forth movement, may be allowed by the fasteners.

In some embodiments, fasteners 1205 include one or more of, for example, clasps, bars, bands, and/or other types of fasteners suitable to hold the sleeve assembly in the jig.

In some embodiments, fasteners 1205 are elastic, and can be stretched for example when the sleeve assembly (inner sleeve 11 and/or outer sleeve 10) is inflated. Alternatively, fasteners 1205 are rigid.

In some embodiments, fasteners 1205 are distributed along a longitudinal axis 1209 of jig 1201. Optionally, the fasteners are equally spaced, for example two fasteners are positioned at a distance 1211 ranging between, for example, 10-30 mm, 5-15 mm, 20-50 mm, or intermediate, larger or smaller ranges from each other.

Alternatively, the fasteners are not equally spaced. In some embodiments, a number of fasteners 1205 and/or a spacing between the fasteners is selected such as to reduce or prevent movement of the sleeve held by the jig.

In some embodiments, jig 1201 is continuous. Alternatively, jig 1201 is non-continuous, for example supporting the sleeve assembly at a plurality of points and/or segments along a longitudinal axis of the sleeve.

In some embodiments, a length 1215 of jig 1201 matches a length of colonoscope 50, for example ranging between 1-3 m, such as 1.2 m, 1.7 m, 2.5 m or intermediate, longer or shorter lengths. A potential advantage of an elongated jig may include facilitating insertion of the colonoscope into the sleeve, for example because the jig supports the sleeve at a plurality of points along the length of the sleeve, enabling fast alignment of the colonoscope.

Figure 13:
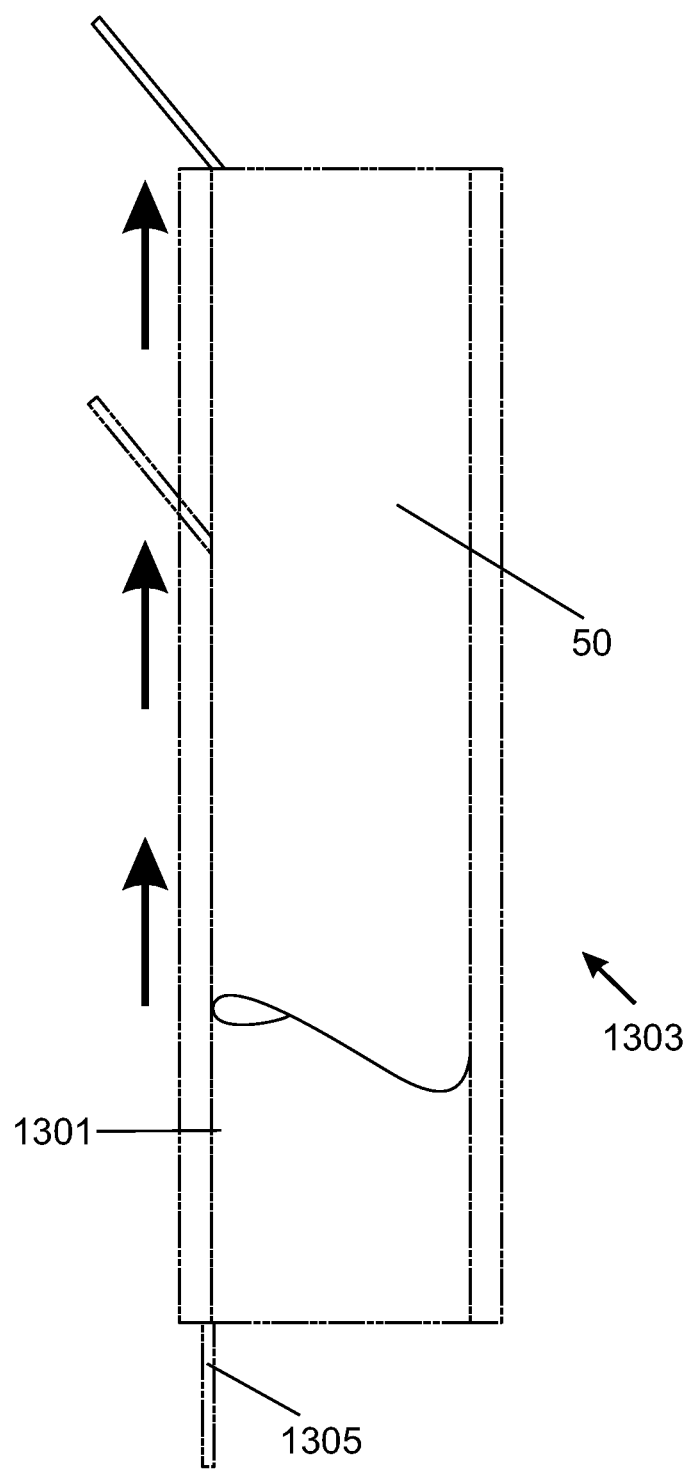
FIG. 13 illustrates an exemplary mechanism for detaching the add-on tubes from the colonoscope, according to some embodiments of the invention.

FIG. 13 illustrates an exemplary mechanism for detaching a colonoscope from a sleeve assembly, for example after completion of the colonoscopy procedure, according to some embodiments of the invention.

In some embodiments, a colonoscope 50 is separated from the add-on tubes, for example after the colonoscope and tubes have been removed from the body. In some embodiments, the add-on tubes are disposed of, and the colonoscope is cleaned, disinfected, and/or otherwise prepared for additional use.

In some embodiments, the separation process of the colonoscope from the add-on tubes is performed in a manner that does substantially damage the colonoscope, for example does not scratch or tear the outer layer of the colonoscope.

In the exemplary mechanism shown in FIG. 13, a string or wire 1301 is embedded in the sleeve assembly 1303. In some embodiments, wire 1301 extends axially along the sleeve. In some embodiments, by pulling on a free end of the wire 1305, for example from a distal point in the sleeve in a proximal direction, the wire tears open the sleeve and the colonoscope can be easily removed.

In some embodiments, for example if sleeve assembly 1303 comprises an outer sleeve and an inner sleeve, wire 1301 may be positioned along the inner and/or the outer sleeve. In an example, a first wire embedded in the outer sleeve is pulled to tear open the outer sleeve, thereby separating the add-on tubes from the colonoscope, and a second wire embedded in the inner sleeve in which the colonoscope is positioned is then pulled to tear open the inner sleeve and release the colonoscope. Additionally or alternatively, the inner and/or outer sleeve are cut open, for example using scissors or a knife. Additionally or alternatively, the inner and optionally the outer sleeve as well are re-inflated, and the colonoscope is pulled out in a similar manner to its insertion to the sleeve.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method for coupling between an endoscope insertion tube and one or more add-on tubes, comprising:
providing a sleeve assembly including:
an inner sleeve surrounded by an outer sleeve; the inner and outer sleeves each defining a longitudinally extending lumen; said inner sleeve and said outer sleeve formed of an elastic material which provides expansion; a diameter of said inner sleeve in a collapsed state being smaller than a diameter of an endoscope insertion tube received therein;
at least one add-on tube extending longitudinally between said inner sleeve and said outer sleeve;
expanding said inner sleeve to a diameter larger than a diameter of an endoscope insertion tube;
positioning the endoscope insertion tube in said longitudinally extending lumen of said expanded inner sleeve; and
collapsing said sleeve inner sleeve, said collapsing causing said outer sleeve to radially contract, thereby bringing said at least one add-on tube radially closer to said endoscope insertion tube, said sleeve assembly then maintaining said at least one add-on tube radially closer to said endoscope insertion tube; and
then inserting the sleeve assembly and the endoscope insertion tube into a body lumen, wherein the collapsing is prior to the inserting of the sleeve assembly into said body lumen.

2. The method according to claim 1, wherein said expanding comprises inflating said inner sleeve.

3. The method according to claim 1, wherein said expanding of said inner sleeve exerts radially outward force on said outer sleeve, causing said outer sleeve to expand.

4. The method according to claim 1, wherein said collapsing comprises suctioning air out of said sleeve assembly or letting airflow out of the sleeve assembly.

5. The method according to claim 1, comprising stretching said sleeve assembly along the longitudinal extent, and wherein collapsing is such that longitudinal tension remains after said at least one add-on-tube is brought radially closer to the endoscope insertion tube.

6. The method according to claim 1, wherein said collapsing fixates a positioning of said at least one add-on tube relative to said endoscope insertion tube.

7. The method according to claim 1, further comprising orienting said at least one add-on tube with respect to said inner sleeve during said collapsing.

8. The method according to claim 1, further comprising removing said endoscope insertion tube from said sleeve assembly by pulling on a thread which extends along said sleeve assembly and protrudes from a distal or proximal end of said sleeve assembly, to tear open the sleeve assembly.

9. The method according to claim 1, further comprising threading said at least one add-on tube to extend longitudinally within said lumen defined by said outer sleeve.

10. The method according to claim 1, wherein said at least one add-on tube is integrated in said sleeve assembly.

11. The method according to claim 1, wherein said positioning comprises reducing friction between said endoscope insertion tube and said sleeve assembly by at least one of:
lubricating an inner surface of said inner sleeve which defines the longitudinally extending lumen, in which said longitudinally extending lumen said endoscope insertion tube is received,
lubricating said endoscope insertion tube, and coating said inner surface of said inner sleeve with a polymer based material suitable for reducing friction.

12. The method according to claim 1, wherein the endoscope insertion tube is sized for insertion to a colon.

13. The method according to claim 1, comprising positioning the sleeve assembly using a jig, so that the endoscope insertion tube can be positioned in the longitudinally extending lumen of said inner sleeve.

14. The method according to claim 1, wherein the collapsing comprises collapsing a plurality of parts of the sleeve assembly separately from one another.

15. The method according to claim 1, further comprising tearing the sleeve assembly and removing said endoscope insertion tube from said sleeve assembly.

16. The method according to claim 1, wherein the at least one add-on tube spirally winds along the longitudinal extent of the sleeve assembly.

17. The method according to claim 1, comprising, following said collapsing, allowing at least some movement between said at least one add-on tube and said endoscope insertion tube.

18. The method according to claim 1, wherein said maintaining comprises maintaining said at least one add-on tube and said endoscope insertion tube within a selected radial boundary.

19. The method according to claim 1, wherein said diameter of said inner sleeve in said collapsed state is at least 5% smaller than a diameter of the endoscope insertion tube.

20. The method according to claim 1, wherein said innser sleeve is coupled to said outer sleeve.

21. The method according to claim 20, wherein a circumferential surface of said outer sleeve is attached to a circumferential surface of said inner sleeve in at least one region along said sleeves.

* * * * *